(12) United States Patent
Itani et al.

(10) Patent No.: US 10,881,713 B2
(45) Date of Patent: Jan. 5, 2021

(54) METHOD AND APPARATUS FOR INTERFACE CONTROL WITH PROMPT AND FEEDBACK

(71) Applicant: Atheer, Inc., Santa Clara, CA (US)

(72) Inventors: Sleiman Itani, East Palo Alto, CA (US); Yu-Hsiang Chen, Cupertino, CA (US); Mohamed Nabil Hajj Chehade, Los Angeles, CA (US); Allen Yang Yang, Richmond, CA (US)

(73) Assignee: Atheer, Inc., Santa Clara, CA (US)

( * ) Notice: Subject to any disclaimer, the term of this patent is extended or adjusted under 35 U.S.C. 154(b) by 1 day.

(21) Appl. No.: 16/271,170

(22) Filed: Feb. 8, 2019

(65) Prior Publication Data

US 2019/0167764 A1  Jun. 6, 2019

Related U.S. Application Data

(63) Continuation of application No. 14/924,837, filed on Oct. 28, 2015, now abandoned.

(51) Int. Cl.
*A61K 38/18* (2006.01)
*A61K 38/17* (2006.01)
*G06F 3/0346* (2013.01)

(52) U.S. Cl.
CPC .......... *A61K 38/1866* (2013.01); *A61K 38/17* (2013.01); *A61K 38/1841* (2013.01); *A61K 38/1858* (2013.01); *A61K 38/1891* (2013.01); *G06F 3/0346* (2013.01)

(58) Field of Classification Search
CPC ................ A61K 38/1866; A61K 38/17; A61K 38/1481; A61K 38/1858; A61K 38/1891; G06F 3/0346
See application file for complete search history.

(56) References Cited

U.S. PATENT DOCUMENTS

| | | | | |
|---|---|---|---|---|
| 5,469,191 A | * | 11/1995 | Smith, III | G06F 3/04892 345/157 |
| 5,655,093 A | * | 8/1997 | Frid-Nielsen | G06F 3/04812 345/169 |
| 5,666,499 A | * | 9/1997 | Baudel | G06F 3/0481 345/157 |

(Continued)

FOREIGN PATENT DOCUMENTS

CN  103631518  3/2014

*Primary Examiner* — Jung-Mu T Chuang
(74) *Attorney, Agent, or Firm* — Miller IP Law, LLC

(57) ABSTRACT

A method, system, apparatus, and/or device that may include a display configured to display a virtual object and a sensor configured to detect a viewer input. The method, system, apparatus, and/or device may include a processing device configured to: associate a first cursor with a first form of a user input; associate a second cursor with a second form of the user input; determine the first form of the user input is associated with a type of the virtual object; display the virtual object with the first cursor to the viewer; detect the viewer input from the viewer of the display; determine whether the form of the viewer input detected by the sensor is the first form, the second form, or an unknown form; and in response to the form of the viewer input being the first form, execute an executable instruction associated with the user input.

20 Claims, 18 Drawing Sheets

(56) References Cited

U.S. PATENT DOCUMENTS

| | | | | |
|---|---|---|---|---|
| 5,793,360 A * | 8/1998 | Fleck | G06F 3/023 | 178/19.01 |
| 5,825,352 A * | 10/1998 | Bisset | G06F 3/044 | 345/173 |
| 5,848,429 A * | 12/1998 | McEntee | G06F 3/038 | 715/255 |
| 5,912,666 A * | 6/1999 | Watson | G06F 3/0481 | 708/303 |
| 5,969,708 A * | 10/1999 | Walls | G06F 3/04842 | 345/157 |
| 6,014,139 A * | 1/2000 | Watson | G06F 3/0481 | 715/764 |
| 6,310,610 B1 * | 10/2001 | Beaton | G06F 3/0488 | 345/173 |
| 6,540,520 B2 * | 4/2003 | Johnson | G09B 7/02 | 434/307 R |
| 7,478,072 B2 * | 1/2009 | Kato | G06F 3/038 | 706/10 |
| 7,698,656 B2 * | 4/2010 | Srivastava | G06F 9/45512 | 715/827 |
| 8,005,275 B2 * | 8/2011 | Mathiassen | G06F 3/03547 | 382/124 |
| 8,135,440 B2 * | 3/2012 | Hong | G02B 27/017 | 455/556.1 |
| 8,147,248 B2 * | 4/2012 | Rimas-Ribikauskas | G09B 19/0053 | 434/118 |
| 8,184,096 B2 * | 5/2012 | Louch | G06F 3/04812 | 345/157 |
| 8,204,768 B1 * | 6/2012 | Grinberg | G06Q 40/08 | 705/4 |
| 8,368,645 B2 * | 2/2013 | Louch | G06F 3/04812 | 345/157 |
| 8,566,717 B2 * | 10/2013 | Markiewicz | G06F 3/04883 | 715/709 |
| 8,622,742 B2 * | 1/2014 | Benko | G06F 3/04883 | 434/118 |
| 8,760,395 B2 * | 6/2014 | Kim | G06T 7/75 | 345/156 |
| 8,897,496 B2 * | 11/2014 | Hildreth | G06F 3/017 | 382/103 |
| 8,972,901 B2 * | 3/2015 | Fletcher | G06F 3/04812 | 715/711 |
| 9,081,177 B2 * | 7/2015 | Wong | G06F 3/013 | |
| 9,229,235 B2 * | 1/2016 | Ballard | G06F 1/163 | |
| 9,229,533 B2 * | 1/2016 | Shigeta | G06F 3/017 | |
| 9,316,827 B2 * | 4/2016 | Lindley | G02B 27/0093 | |
| 9,383,816 B2 * | 7/2016 | Hennelly | G09G 5/10 | |
| 9,483,144 B1 * | 11/2016 | Usey | G06F 3/0436 | |
| 10,409,443 B2 * | 9/2019 | Wright | G06F 3/013 | |
| 2001/0044098 A1 * | 11/2001 | Johnson | G09B 7/02 | 434/323 |
| 2003/0201982 A1 * | 10/2003 | Iesaka | G06F 1/1616 | 345/168 |
| 2005/0216551 A1 * | 9/2005 | Sirstins | H04M 3/5183 | 709/202 |
| 2006/0026572 A1 * | 2/2006 | Srivastava | G06F 9/45512 | 717/136 |
| 2006/0101354 A1 * | 5/2006 | Hashimoto | G06F 3/0482 | 715/863 |
| 2006/0136840 A1 * | 6/2006 | Keely, Jr. | G06F 3/0483 | 715/808 |
| 2006/0210958 A1 * | 9/2006 | Rimas-Ribikauskas | G09B 7/00 | 434/362 |
| 2007/0177803 A1 * | 8/2007 | Elias | G06F 3/04883 | 382/188 |
| 2008/0129686 A1 * | 6/2008 | Han | G06F 3/0482 | 345/156 |
| 2008/0163130 A1 * | 7/2008 | Westerman | G06F 3/04883 | 715/863 |
| 2008/0178126 A1 * | 7/2008 | Beeck | G06F 3/017 | 715/863 |
| 2009/0140978 A1 * | 6/2009 | Louch | G06F 3/04812 | 345/157 |
| 2009/0228828 A1 * | 9/2009 | Beatty | G06F 3/0488 | 715/786 |
| 2009/0319894 A1 * | 12/2009 | Markiewicz | G06F 3/04883 | 715/702 |
| 2011/0093819 A1 | 4/2011 | Irvine | | |
| 2011/0117535 A1 * | 5/2011 | Benko | G06F 3/04883 | 434/365 |
| 2011/0216075 A1 * | 9/2011 | Shigeta | G06F 3/017 | 345/473 |
| 2012/0131513 A1 * | 5/2012 | Ansell | G06F 3/04883 | 715/863 |
| 2012/0229379 A1 * | 9/2012 | Louch | G06F 3/04812 | 345/157 |
| 2013/0038537 A1 | 2/2013 | Nashii et al. | | |
| 2013/0055143 A1 | 2/2013 | Martin et al. | | |
| 2013/0080916 A1 * | 3/2013 | Lopez | H04N 5/445 | 715/753 |
| 2013/0335301 A1 * | 12/2013 | Wong | G06F 3/04815 | 345/8 |
| 2014/0125589 A1 | 5/2014 | Kim et al. | | |
| 2014/0164934 A1 | 6/2014 | Yang | | |
| 2015/0070387 A1 | 3/2015 | Schmalsteig et al. | | |
| 2015/0153922 A1 * | 6/2015 | Ballard | H04L 67/18 | 345/156 |
| 2016/0098579 A1 * | 4/2016 | Ballard | G06F 1/163 | 726/27 |
| 2016/0378294 A1 * | 12/2016 | Wright | G06F 3/04815 | 715/851 |
| 2017/0139568 A1 * | 5/2017 | Itani | G06F 3/04883 | |
| 2017/0351338 A1 | 12/2017 | Bondan et al. | | |
| 2017/0374204 A1 * | 12/2017 | Wang | G06Q 20/349 | |
| 2018/0203503 A1 * | 7/2018 | Chehade | G06F 3/011 | |
| 2018/0341760 A1 * | 11/2018 | Frempong | H04L 63/0807 | |
| 2019/0109849 A1 * | 4/2019 | Frempong | H04L 63/10 | |
| 2019/0167764 A1 * | 6/2019 | Itani | G06F 3/0481 | |
| 2019/0347189 A1 * | 11/2019 | Chen | G06F 11/3692 | |

* cited by examiner

METHOD AND APPARATUS FOR INTERFACE CONTROL WITH PROMPT AND FEEDBACK

CROSS-REFERENCE TO RELATED APPLICATION

This application is a continuation of U.S. patent application Ser. No. 14/942,837, filed Nov. 16, 2015, the contents of which is incorporated by reference for all intents and purposes.

FIELD OF THE INVENTION

This disclosure relates to controlling an interface with prompts for input and/or feedback regarding that input. More particularly, the disclosure relates to outputting graphical prompts such as cursors indicating to a user the type of input that is anticipated and providing graphical feedback to the user as to whether the user input that is detected corresponds with the user input that is anticipated.

DESCRIPTION OF RELATED ART

Cursors may serve to indicate where and/or when the input is to be entered. For example, a cursor may be displayed within a digital text document so as indicate where text would be added to that document if a user were to enter text at that time.

However, problems may manifest if variables other than time and/or place are relevant. For example, if a two or more distinct types of input may be entered, it may be unclear from a cursor as to which type of input is appropriate even if the time and place for entering the input are visually identified by the presence and/or position of the cursor. It may not be clear to the user that he or she is entering suitable input until after input has been entered; an indication of time and place may not be sufficient to either confirm correct input or advise of incorrect input.

Thus even if a cursor may serve to indicate the time and place at which input is to be entered, a degree of ambiguity may remain. As inputs become more varied, such issues may become increasingly problematic. For example, with two types of input distinguishing an appropriate situation for each may be relatively easy, and even a random guess may be expected to be correct 50% of the time, and distinguishing, by contrast with three, four, or more types of input determining the appropriate input type may be more difficult, and random guessing may be less effective.

BRIEF SUMMARY OF THE INVENTION

This disclosure contemplates a variety of systems, apparatus, methods, and paradigms for prompting, confirming, and/or providing feedback on input.

In one embodiment, a machine-implemented method is provided that includes establishing user inputs in a processor, establishing graphical cursors in the processor, and associating each of the cursors with at least one of the user inputs in the processor. The method includes anticipating an anticipated user input in the processor and outputting the cursor associated with the anticipated user input to a graphical display. Each of the graphical cursors is graphically distinctive from the other cursors and is graphically indicative of the user inputs associated therewith, so as to identify to a viewer of the graphical display the anticipated user input.

The method may include establishing a base form and an engaged form for at least some of the graphical cursors, outputting the base form of the cursor associated with the anticipated user input to the graphical display, and detecting a detected user input. If the detected user input corresponds with the anticipated user input associated with the outputted cursor, the method includes outputting the engaged form of the cursor associated with the anticipated user input to the graphical display, so as to confirm to the viewer a correspondence between the anticipated user input and the detected user input.

The method may include outputting to the graphical display a graphical emphasis of the base form of the cursor associated with the anticipated user input so as to indicate to the viewer a non-correspondence between the anticipated user input and the detected user input if the detected user input does not correspond with the anticipated user input. The method may include outputting to the graphical display an error indication so as to indicate to the viewer a non-correspondence between the anticipated user input and the detected user input if the detected user input does not correspond with the anticipated user input.

The method may include establishing a base form and a hover form for at least some of the graphical cursors, outputting the base form of the cursor associated with the anticipated user input to the graphical display, and detecting a detected user hover. If the detected user hover corresponds with the anticipated user input associated with the outputted cursor, the method includes outputting the hover form of the cursor associated with the anticipated user input to the graphical display, so as to confirm to the viewer a correspondence between the anticipated user input and the detected user hover.

The method may include outputting to the graphical display a graphical emphasis of the base form of the cursor associated with the anticipated user input so as to indicate to the viewer a non-correspondence between the anticipated user input and the detected user hover if the detected user hover does not correspond with the anticipated user input. The method may include outputting to the graphical display an error indication so as to indicate to the viewer a non-correspondence between the anticipated user input and the detected user hover if the detected user hover does not correspond with the anticipated user input.

The user inputs may include hand gesture inputs. The user inputs may include free space hand gesture inputs.

For at least one of the cursors, the base form thereof may be graphically hollow and the engaged form thereof is graphically filled. For at least one of the cursors, the hover form thereof may be graphically compacted compared to the base form thereof.

The user inputs may include a single touch input and the cursors may include a single touch cursor associated with the single touch input, with the single touch cursor being graphically indicative of a one-point touch to a designated position in space. The single touch cursor may include a circle with crosshair marks disposed around a periphery thereof, the circle being graphically indicative of the designated position and the one-point touch thereto.

The user inputs may include a double touch input and the cursors may include a double touch cursor associated with the double touch input, with the double touch cursor being graphically indicative of a two-point touch to a designated position in space.

The user inputs may include a single touch input and the cursors may include a single touch cursor associated with the single touch input, with the single touch cursor including a circle with crosshair marks disposed around a periphery thereof, and the double touch cursor including a circle larger than the single touch cursor circle with crosshair marks disposed around a periphery thereof, with the double touch cursor circle being graphically indicative of the designated position and the double touch cursor circle being larger being graphically indicative of the two-point touch thereto.

The double touch cursor may include two at least partial circles mutually connected with crosshair marks disposed around a periphery thereof, with the at least partial circles being graphically indicative of the designated position and the two at least partial circles being graphically indicative of the two-point touch thereto.

The double touch cursor may include two circles mutually proximate with crosshair marks disposed around a perimeter thereof, with the circles being graphically indicative of the designated position, and the two circles being graphically indicative of the two-point touch thereto.

The double touch cursor may include a circle with paired crosshair marks disposed around a periphery thereof, with the circle being graphically indicative of the designated position and the double crosshair marks being graphically indicative of the two-point touch thereto.

The user inputs may include a single point directional swipe input and the cursors may include a single point directional swipe cursor associated with the single point directional swipe input, with the single point directional swipe cursor being graphically indicative of a one-point swipe in a designated direction.

The single point directional swipe cursor may include a circle with at least one arrow disposed around a periphery thereof, with the at least one arrow being graphically indicative of the designated direction and the circle being graphically indicative of the one-point swipe in the designated direction.

The user inputs may include a double point directional swipe input and the cursors may include a double point directional swipe cursor associated with the double point directional swipe input, with the double point directional swipe cursor being graphically indicative of a two-point swipe in a designated direction.

The user inputs may include a single point directional swipe input and the cursors may include a single point directional swipe cursor associated with the single point directional swipe input, with the single point directional swipe cursor including a circle with at least one arrow disposed around a periphery thereof, and the double point directional swipe cursor including a circle larger than the single point directional swipe cursor circle with at least one arrow disposed around a periphery thereof. The at least one arrow disposed around the periphery of the double point circle may be graphically indicative of the designated direction and the double point circle being larger may be graphically indicative of the two-point swipe in the designated direction.

The double point directional swipe cursor may include two at least partial circles mutually connected with at least one arrow disposed around a periphery thereof, with the arrow being graphically indicative of the designated direction and the two at least partial circles being graphically indicative of the two-point swipe in the designated direction.

The double point directional swipe cursor may include two circles mutually proximate with at least one arrow disposed around a periphery thereof, with the arrow being graphically indicative of the designated direction and the two circles being graphically indicative of the two-point swipe in the designated direction.

The double point directional swipe cursor may include a circle with at least one pair of arrows disposed around a periphery thereof, with the pair of arrows being graphically indicative of the designated direction and the two-point swipe in the designated direction.

The user inputs may include a single point press input and the cursors may include a single point press cursor associated with the single point press input, with the single point press input cursor being graphically indicative of a one-point press at a designated position.

The one finger press cursor may include a circle, with the circle being graphically indicative of the designated position and the one-point press thereto.

The user inputs may include a double point press input and the cursors may include a double point press cursor associated with the double point press input, with the double point press input cursor being graphically indicative of a two-point press at a designated position.

The user inputs may include a single point press input and the cursors may include single point press cursor associated with the single point press input, with the single point press cursor including a circle and the double point press cursor including a circle larger than the single point directional swipe cursor circle, and with the double point press circle being graphically indicative of the designated position and the double point press circle being larger being graphically indicative of the two-point touch thereto.

The double point press cursor may include two at least partial circles mutually connected, with the at least partial circles being graphically indicative of the designated position and the two at least partial circles being graphically indicative of the two-point touch thereto.

The double point press cursor may include two circles mutually proximate, with the circles being graphically indicative of the designated position and the two circles being graphically indicative of the two-point touch thereto.

The user inputs may include a single point press and hold input and the cursors may include a single point press and hold cursor associated with the single point press and hold input, with the single point press and hold input cursor being graphically indicative of a one-point press and hold at a designated position.

The one finger press and hold cursor may include a circle with at least one concentric ring disposed thereabout, with the circle being graphically indicative of the designated position and the one-point press thereto, and the concentric ring being graphically indicative of the press and hold.

The inputs may include a double point press and hold input and the cursors may include a double point press and hold cursor associated with the double point press and hold input, with the double point press and hold input cursor being graphically indicative of a two-point press at a designated position.

The user inputs may include a single point press and hold input and the cursors may include single point press and hold cursor associated with the single point press and hold input, with the single point press and hold cursor including a circle with at least one concentric ring disposed thereabout and the double point press and hold cursor including a circle larger than the single point press and hold cursor circle with at least one concentric ring disposed thereabout, and with the double point press circle being graphically indicative of the designated position, the double point press circle being larger is graphically indicative of the two-point touch thereto, and the at least one concentric ring being graphically indicative of the press and hold.

The double point press cursor may include two at least partial circles mutually connected with two corresponding at least partial concentric rings disposed thereabout, with the at least partial circles being graphically indicative of the designated position, the two at least partial circles being graphically indicative of the two-point touch thereto, and the at least partial concentric rings being graphically indicative of the press and hold.

The double point press cursor may include two circles mutually proximate with two corresponding concentric rings disposed thereabout, with the circles being graphically indicative of the designated position, the two circles being graphically indicative of the two-point touch thereto, and the concentric rings being graphically indicative of the press and hold.

The user inputs may include a pinch in input and the cursors may include a pinch in cursor associated with the pinch in input, with the pinch in cursor being graphically indicative of a two-point distance closing motion.

The pinch in cursor may include two arrows mutually proximate and oriented point to point, with the arrows being graphically indicative of the two-point distance closing motion.

The pinch in cursor may include a visible perimeter enclosing the arrows, with the visible perimeter enclosing the arrows is graphically indicative of the two-point distance closing motion.

The pinch in cursor may include two circles mutually proximate.

The pinch in cursor may include a visible perimeter enclosing the circles, with the visible perimeter enclosing the circles being graphically indicative of the two-point distance closing motion.

The user inputs may include a pinch out input and the cursors may include a pinch out cursor associated with the pinch out input, with the pinch out cursor being graphically indicative of a two-point distance opening motion.

The pinch out cursor may include two arrows mutually proximate and oriented base to base, with the arrows being graphically indicative of the two-point distance opening motion.

The pinch out cursor may include a visible perimeter between the arrows, with the visible perimeter between the arrows being indicative of the two-point distance opening motion.

The pinch out cursor may include two circles mutually proximate.

The pinch out cursor may include a visible perimeter between the circle, with the visible perimeter between the circles being indicative of the two-point distance opening motion.

In another embodiment, a machine-implemented method is provided that includes establishing a one-finger input, a two-finger input, a pinch-in input, and a pinch-out input in a processor, the user inputs including free space hand gesture inputs. The method includes establishing a base form, a hover form, an engaged press form, and an engaged press-and-hold form for the one-finger input in the processor, establishing a base form, an engaged press form, and an engaged swipe form for the two-finger input in the processor, establishing a base form and an engaged form for the pinch-out input in the processor, and establishing a base form and an engaged form for the pinch-in input in the processor.

The method includes establishing a plurality of graphical cursors and associating each of the cursors with at least one of the user inputs in the processor.

The graphical cursors include a base form one-finger input graphical cursor including a hollow circle with dashed crosshair marks disposed around a periphery thereof associated with the base form of the one-finger input, a hover form one-finger input graphical cursor including a hollow circle with contracted dashed crosshair marks disposed around a periphery thereof associated with the hover form of the one-finger input, an engaged form one-finger press input graphical cursor including a filled circle associated with the engaged press form of the one-finger input, and an engaged form one-finger press-and-hold input graphical cursor including a filled circle with at least one concentric circle thereabout associated with the engaged press-and-hold form of the one-finger input.

The graphical cursors include a base form two-finger input graphical cursor including a hollow circle with arrow marks disposed around a periphery thereof associated with the base form of the two-finger input, an engaged form two-finger press input graphical cursor including a filled circle with arrow marks disposed around a periphery thereof associated with the engaged press form of the two-finger input, and an engaged form two-finger swipe input graphical cursor including a filled circle with arrow marks disposed around a periphery thereof with at least one of the arrow marks including at least two arrows associated with the engaged press-and-hold form of the two-finger input.

The graphical cursors also include a base form pinch-out input graphical cursor including a hollow dashed circle with arrow marks disposed around a periphery thereof and pointing outward therefrom associated with the base of the pinch-out input, an engaged form pinch-out input graphical cursor including a filled dashed circle with arrow marks disposed around a periphery thereof and pointing outward therefrom with each of the arrow marks including at least two arrows associated with the engaged form of the pinch-out input, a base form pinch-in input graphical cursor including a hollow dashed circle with arrow marks disposed within a periphery thereof and pointing inward therefrom associated with the base of the pinch-in input, and a base form pinch-in input graphical cursor including a filled dashed circle with arrow marks disposed within a periphery thereof and pointing inward therefrom with each of the arrow marks including at least two arrows associated with the engaged form of the pinch-in input.

Each of the graphical cursors is graphically distinctive from the other cursors and is and graphically indicative of the user inputs associated therewith, so as to identify to a viewer of the graphical display the anticipated user input.

The method further includes anticipating an anticipated user input in the processor and outputting to a graphical display the base form of the cursor associated with the anticipated user input.

The method includes detecting a user hover, and outputting to the graphical display the hover form of the cursor associated with the anticipated user input, so as to confirm to the viewer a match between the anticipated user input and the detected user hover if the detected user hover corresponds with the anticipated user input associated with the outputted cursor and the outputted cursor includes the hover form.

The method further includes detecting a user input, and outputting to the graphical display the engaged form of the cursor associated with the anticipated user input, so as to confirm to the viewer a match between the anticipated user input and the detected user input, if the detected user input corresponds with the anticipated user input associated with the outputted cursor and the outputted cursor includes the engaged form.

In another embodiment, an apparatus is provided that includes a processor, a graphical display in communication with the processor, and an input receiver in communication with the processor. The apparatus includes a plurality of user input definitions for user inputs disposed on the processor and a plurality of graphical cursor definitions for graphical cursors disposed on the processor, each graphical cursor being associated with at least one of the user inputs. Each of the graphical cursors is graphically distinctive from the other cursors and is and graphically indicative of the user inputs associated therewith. The apparatus includes a user input anticipator adapted to anticipate anticipated user input to the input receiver, and an outputter adapted to output the graphical cursor associated with the anticipated user input to the graphical display, so as to identify to a viewer of the graphical display the anticipated user input.

At least some of the input definitions may include a base form and an engaged form. The apparatus may include a user input detector adapted to detect a detected user input, and a user correspondence determiner adapted to determine whether the detected user input corresponds with the anticipated user input. The outputter may be adapted to output the engaged form of the cursor associated with the anticipated user input to the graphical display if the detected user input corresponds with the anticipated user input, so as to confirm to the viewer a correspondence between the anticipated user input and the detected user input.

At least some of the input definitions may include a base form and a hover form. The apparatus may include a user hover detector adapted to detect a detected user hover, a correspondence determiner adapted to determine whether the detected user input corresponds with the anticipated user input. The outputter may be adapted to output the hover form of the cursor associated with the anticipated user input to the graphical display if the detected user hover corresponds with the anticipated user input, so as to confirm to the viewer a correspondence between the anticipated user input and the detected user hover.

The graphical display may include a stereo near-eye display, the input receiver may include an imager, and the apparatus may include a frame adapted to be worn on a head of the viewer, the graphical display and the input receiver being disposed thereon. The frame may be configured such that when the viewer wears the frame the stereo near-eye display is disposed proximate and facing eyes of the viewer and the input receiver is disposed so as to receive input from in front of the viewer.

In another embodiment, an apparatus is provided that includes a processor, means for outputting graphical content to a viewer in communication with the processor, means for establishing a plurality of user inputs in the processor, and means for establishing a plurality of graphical cursors and associating each of the cursors with at least one of the user inputs in the processor. The apparatus also includes means for anticipating an anticipated user input and means for outputting the cursor associated with the anticipated user input. Each of the graphical cursors is graphically distinctive from the other cursors and is and graphically indicative of the user inputs associated therewith, so as to identify to a viewer of the graphical display the anticipated user input.

BRIEF DESCRIPTION OF THE SEVERAL VIEWS OF THE DRAWINGS

Like reference numbers generally indicate corresponding elements in the figures.

DETAILED DESCRIPTION OF THE INVENTION

Figure 1:
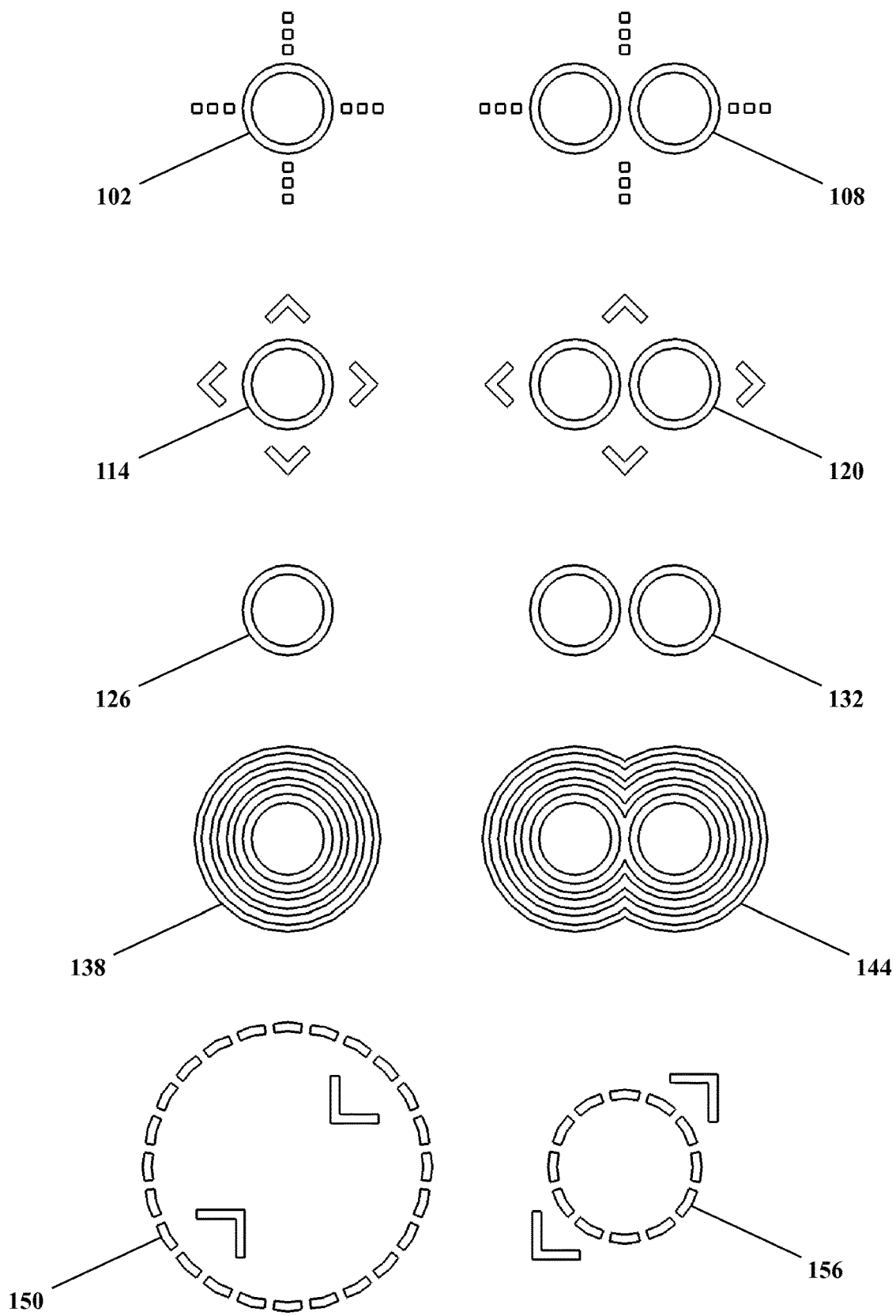
FIG. 1 shows example cursors for prompting various inputs, in graphical form.

In at least certain embodiments, cursors are provided (e.g. displayed to a user) that graphically indicate what input(s) may be anticipated, and/or that graphically indicate whether inputs being entered by a user match or do not match the inputs that are anticipated. More colloquially, the user is shown a cursor form that suggests the "right" input; if the user enters the "right" input the user is shown a cursor form that confirms detection of that "right" input, while if the user enters the "wrong" input the user is shown a cursor form that indicates detection of that "wrong" input.

Broadly speaking, presenting a user with a cursor regardless of the cursor's form may provide the user with information regarding where and/or when input from that user will be accepted. For example, consider a digital "desktop" environment wherein a user may click a mouse to open files, initiate programs, activate functions, etc. A cursor may be displayed in the form of an arrow to indicate where and when a mouse click, tap, etc. would be received if applied by the user.

When the type of input that a user may apply in a given situation is limited, then designating time and position with a cursor may provide sufficient guidance to a user to reliably enter suitable inputs. For example, considering a mouse where the only input available is "click", then displaying a cursor that indicates the position at which a click will be applied at a given time may be sufficient for the user to apply click inputs.

However, if a user may apply multiple distinct inputs to an interface, merely indicating a position for a given time may leave some ambiguity for the user. For example, consider an arrangement wherein free space gesture inputs are used to control a system, such as a head mounted display presenting virtual reality, augmented reality, etc. to a user. If the system can discriminate between a gesture carried out with one finger and a similar gesture carried out with two fingers, then the number of gestures available for use as inputs is greater. However, if several different gestures may be used as inputs, then some of those inputs may only be suitable in certain circumstances, and it may not be clear to the user which input(s) are suitable.

Such ambiguity may be ameliorated or avoided by providing a user with indications as to which input may be most suitable for a given time and place. In certain embodiments, such an indication may be provided graphically, through the user of a suite of cursors rather than a single cursor. This may be in addition to the use of a cursor to show when and/or where input will be received or applied. For example, one cursor in a suite may indicate that gesture inputs made using one finger are expected at a particular time and location, while another cursor in the suite may indicate that gesture inputs made using two fingers are expected.

In more colloquial terms, where a time-and-place only cursor may advise a user that "your input will go here", an input-type cursor may further advise a user that "and a two-finger input is suitable". As the number of possible inputs increases, such additional guidance may be increasingly useful.

A distinction is drawn between cursors that merely depict a type of input that will be entered. For example, an image editing program might display a cursor in the form of a pen nib pattern to identify that a "pen" tool has been selected. However, this does not indicate an anticipated form of input to the user, but rather is specific to what tool, in fact, will be used. No matter what the user does with the "pen" tool, a color will be applied in the form of a pen line onto the image file. The user has only the option to either enter pen input or choose a different tool. No feedback regarding whether the user applied the "right input" or the "wrong input" is possible, since the user is constrained only to pen input; the user cannot apply anything else so there is no "right input" or "wrong input".

By contrast, in various embodiments, as described herein a user may be shown a cursor graphically indicative of some type of anticipated input (or recommended input, etc.). The user thus may be advised of a suitable input, but still may choose to enter some different input. In addition, the user may be advised as to whether the input they enter (or begin to enter, etc.) is suitable, again by being shown a cursor that is graphically indicative of the correct input, or an incorrect (or at least unexpected) input, etc.

Thus, rather than merely showing what must happen, various embodiments may prompt a user regarding input that should be entered, and/or provide feedback to the user regarding their input.

Typically, such prompting and feedback may utilize a group of cursors, and/or one or more cursors with multiple different forms. Collectively, such a group of cursors and forms thereof may be referred to as a suite.

Cursors within a suite may be visually distinct, so as to indicate to a user which inputs may be suitable. With reference to FIG. 1, therein is shown several cursors 102 through 156. If all of the illustrated cursors 102 through 156 were used together in a particular system, the cursors 102 through 156 collectively may be considered to be a suite.

However, the cursors 102 through 156 are shown as examples and are not required to be used together. Likewise, the example cursors 102 through 156 should not be considered limiting, and other arrangements may be equally suitable.

Various levels of discrimination may be suitable. In FIG. 1, a general one-finger cursor 102 and a general two-finger cursor 108 are shown. (Where additional cursors 114 through 156 are present, cursors 102 and 108 may be further specified, e.g. as a one-finger touch cursor 102 and a two-finger touch cursor 108, though this is an example only.)

Typically though not necessarily, the one-finger cursor 102 may be associated with one-finger gesture inputs (e.g. being displayed one one-finger gestures is suitable, anticipated, etc.) and the two-finger cursor may be associated with two-finger gesture inputs. In certain embodiments only cursors 102 and 108 (or analogs thereof) may be used; that is, it may be that cursors 102 and 108 discriminate between one-finger and two-finger inputs, and indicate to a user whether a one-finger input or a two-finger input is suitable and/or anticipated at some time and place, without necessarily providing further information as two what specific one-finger and two-finger inputs may be suitable and/or anticipated. The one-finger cursor 102 and two-finger cursor 108 may form a suite in themselves, without necessarily including other cursors (such as cursors 114 through 156 also in FIG. 1). However, as described below and as visible in FIG. 1, additional cursors 114 through 156 also may be present.

As may be seen, the one-finger cursor 102 includes a hollow circle with dashed crosshairs extending in cardinal directions from the center thereof. The two-finger cursor 108 includes two hollow circles, again with dashed crosshairs extending in cardinal directions from the center thereof. The one-finger cursor 102 and two-finger cursor 108 are graphically distinctive from one another (e.g. the one-finger cursor 102 having one circle while the two-finger cursor 108 has two circles), and are graphically indicative of the user inputs associated therewith (e.g. a single circle indicating the use of one fingertip for the one-finger cursor 102, and two circles indicating the use of two fingertips for the two-finger cursor 108).

It is noted that terms such as "one-finger" and "two-finger" are used herein in places as examples, for clarity. More broadly, inputs and/or cursors associated with inputs may be considered as exhibiting "one point of manipulation", "two points of manipulation", etc. The use of fingers and/or fingertips as points of manipulation may be suitable for certain embodiments. However, embodiments are not limited only to fingers or fingertips, and other arrangements, including but not limited to styluses, knuckles (as opposed to fingertips), full hands, etc. may be equally suitable.

Still, with reference to FIG. 1, a one-finger swipe cursor 114 and a two-finger swipe cursor 120, a one-finger press cursor 126 and a two-finger press cursor 132, a one-finger press-and-hold cursor 138 and a two-finger press-and-hold cursor 144, a pinch in cursor 150 and a pinch out cursor 156 also are shown. As noted, not all cursors 102 through 156 must be present in a given embodiment. However, the use of several cursors 102 through 156 as shown in FIG. 1 may provide greater discrimination between different possible inputs, and thus more guidance to a user as to what inputs are suitable, anticipated, required, etc.

Where one-finger cursor 102 and two-finger cursor 108 may be associated with general one and two-finger inputs (or to one and two-finger inputs not otherwise specified, etc.), other cursors 114 through 156 may be specific to more particular inputs.

For example, the one-finger swipe cursor 114 and two-finger swipe cursor 120 may be associated with swipes, that is, moving one or two fingertips respectively through space as inputs. As may be seen, the one-finger swipe cursor 114 includes a hollow circle with arrows arranged in cardinal directions around the center thereof. The two-finger swipe cursor 120 includes two hollow circles, again with arrows arranged in cardinal directions around the center thereof. The one-finger swipe cursor 114 and two-finger swipe cursor 120 are graphically distinctive from one another and from the other cursors 102, 108, and 126 through 156 in FIG. 1 and are graphically indicative of the user inputs associated therewith (e.g. a single circle indicating the use of one fingertip for the one-finger swipe cursor 114 with arrows indicating motions, and two circles indicating the use of two fingertips for the two-finger swipe cursor 120 again with arrows indicating motions).

Similarly, the one-finger press cursor 126 and two-finger press cursor 132 may be associated with presses, that is, applying one or two fingertips to some point as inputs. As may be seen, the one-finger press cursor 126 includes a hollow circle without further marking. The two-finger press cursor 132 includes two hollow circles, again without further marking. The one-finger press cursor 126 and two-finger press cursor 132 are graphically distinctive from one another and from the other cursors 102 through 132 and 138 through 156 in FIG. 1, and are graphically indicative of the user inputs associated therewith (e.g. a single circle indicating the use of one fingertip for the one-finger press cursor 126 and two circles indicating the use of two fingertips for the two-finger press cursor 132, not otherwise marked to indicate a simple press).

Likewise, the one-finger press-and-hold cursor 138 and two-finger press-and-hold cursor 144 may be associated with presses-and-holds, that is, applying one or two fingertips to some point in space and remaining there for some period, as inputs. As may be seen, the one-finger press-and-hold cursor 138 includes a hollow circle with three concentric rings encompassing the circle, and the two-finger press-and-hold cursor 144 includes two hollow circles, with three concentric partial rings encompassing both circles. The one-finger press-and-hold cursor 138 and two-finger press-and-hold cursor 144 are graphically distinctive from one another and from the other cursors 102 through 132, 150, and 156, and are graphically indicative of the user inputs associated therewith (e.g. for the one-finger press-and-hold cursor 138 a single circle indicating the use of one fingertip for the press and concentric rings indicating the hold, for the two-finger press-and-hold cursor 144 two circles indicating the use of two fingertips and concentric partial rings indicating the hold).

In addition, the pinch in cursor 150 and pinch out cursor 156 may be associated with pinches, that is, moving two fingertips towards or apart from one another. As may be seen, the pinch in cursor 150 includes a dashed hollow circle enclosing two arrows pointing toward one another, while the pinch out cursor 156 includes a dashed hollow circle between two arrows pointing away from one another.

The pinch in cursor 150 and pinch out cursor 156 are graphically distinctive from one another and from the other cursors 102 through 144, and are graphically indicative of the user inputs associated therewith (e.g. for the pinch in cursor 150 a large dashed circle indicating a broad initial spread with arrows indicating inward motion, while for the pinch out cursor 156 a small dashed circle indicating a narrow initial spread with arrows indicating outward motion).

As may be seen in FIG. 1, the one-finger cursors 102, 114, 126, and 138 are graphically similar to the corresponding two-finger cursors 108, 120, 132, and 144. That is, the one-finger swipe cursor 114 is graphically similar to the two-finger swipe cursor 120, with both including one or more circles and arrows arranged in cardinal directions, though the two-finger swipe cursor 120 has two circles while the one-finger swipe cursor 114 has one circle. This may be useful for certain embodiments, for example, so as to provide similar and/or familiar graphical information to the user for inputs having similar associations. However, such similarity is not required, and other arrangements may be suitable.

Likewise, the one-finger cursors 102, 114, 126, and 138 are graphically similar to one another (though still graphically distinct), and the two-finger cursors 108, 120, 132, and 144 also are graphically similar to one another (though still graphically distinct). For example, each of the one-finger cursors 102, 114, 126, and 138 exhibits one central circle, and each of the two-finger cursors 108, 120, 132, and 144 exhibits two circles side-by-side. Again, this may be useful for certain embodiments, for example, so as to provide similar and/or familiar graphical information to the user for inputs using similar hand configurations. However, such similarity also is not required, and other arrangements may be suitable.

Further, the pinch in cursor 150 and pinch out cursor 156 are graphically similar to one another (though still graphically distinct). For example, the pinch in cursor 150 and pinch out cursor 156 each exhibit a dashed circle with arrows. This may be useful for certain embodiments, for example, so as to provide similar and/or familiar graphical information to the user for inputs using similar motions and/or performing similar (though in the case of cursors 150 and 156, reversed) functions. However, such similarity also is not required, and other arrangements may be suitable.

Graphical similarities based on features such as the number of fingers in a gesture, the associated inputs, and/or the type of motion (if any) may be suitable for certain embodiments but are not required. Graphical similarities based on other features, or no such graphical similarities, also may be suitable.

Considering FIG. 1 collectively, the cursors 102 through 156 shown therein may provide prompts for a range of different types of input: non-specified one-finger and two-finger inputs, one-finger and two-finger swipes, one-finger and two-finger presses, one-finger and two-finger press-and-holds, and inward and outward pinches. Thus, a user may be prompted with a considerable granularity as to what inputs are anticipated, suitable, required, etc. at a given time and place, by graphically indicating the appropriate inputs through the display of a cursor associated with those appropriate inputs.

It is emphasized that the particular appearances, forms, etc. of the cursors 102 through 156 as shown in FIG. 1 (and likewise in other illustrations herein) are examples only and are not limiting. The individual appearances of various cursors 102 through 156 may be considered decorative; however, the association of those cursors that have particular appearances with particular inputs nevertheless may be useful. That is, regardless of what (for example) a pinch out cursor 156 looks like, the existence and graphical distinctiveness of a pinch out cursor 156 may enable prompting a user for a particular type of input.

It is noted that the term "graphically indicative" may be a matter of interpretation, experience, culture, etc. Graphical indications of various motions, functions, etc. may vary, and may even be arbitrary (e.g. being defined for a particular suite of cursors). For example, while the cardinal arrows in the one-finger swipe cursor 114 and two-finger swipe cursor 120 in FIG. 1 may be considered to graphically indicate motion, this is an example only. Shapes, arrangements, etc. that may be understood as indicating motion may vary. So long as motion is graphically indicated in some fashion, whether arrows, rays, motion lines, etc. are used may vary from one embodiment to another. Likewise, whether circles are used to indicate fingertips (or other points), etc. also may vary. So long as the functionality in conveying information is achieved, the cosmetic appearance of whatever "vehicle" is used to indicate that information is not limited.

In particular, it is noted that though the various cursors 102 through 156 in FIG. 1 are shown as being distinguished by shape, other distinctions may be equally suitable. For example, cursors may be distinguished in whole or in part by color, through animation, through audio cues, etc.

In FIG. 1, examples are shown of various cursors 102 through 156 as distinguished by the type of input. That is, a one-finger swipe cursor 114 may be displayed to a user to prompt a one-finger swipe input. However, cursors also may have two or more forms, so as to provide additional information to the user, including but not limited to confirmation that the input from the user matches the anticipated input. For example, a cursor may have a base form, as may be displayed to a user to prompt a type of input from the user, and also may have an engaged form as may be displayed while a user enters input matching the anticipated input (and/or for some period after entering input matching the anticipated input.

Figure 2:
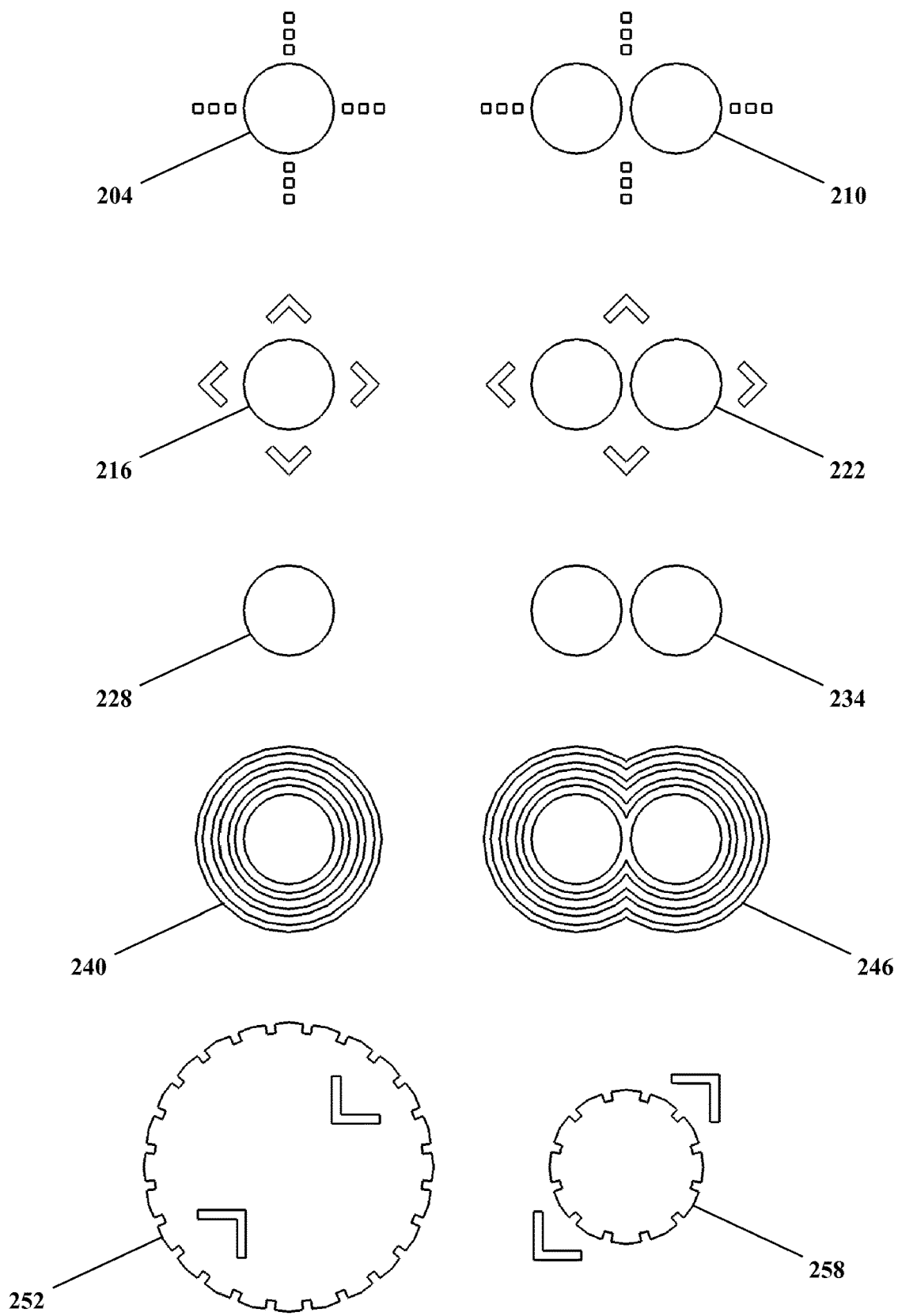
FIG. 2 shows example cursors for providing feedback regarding various inputs being enabled, in graphical form.

With reference now to FIG. 2, engaged forms of cursors 204 through 258 at least somewhat similar to the cursors 102 through 156 in FIG. 1, though not identical thereto. If the cursors 102 through 156 in FIG. 1 are considered to represent base forms, the cursors 204 through 258 may be considered to represent engaged forms.

As may be seen, each of the engaged form cursors 204 through 258 in FIG. 2 are at least somewhat similar to the base form cursors 102 through 156 in FIG. 1, in terms of general shape and configuration. However, where the base form cursors 102 through 156 in FIG. 1 include hollow circles, the engaged form cursors 204 through 258 in FIG. 2 include solid circles. More colloquially, in FIG. 2 the cursors 204 through 258 are "filled in".

The cursors 204 through 258 include an engaged form one-finger cursor 204, an engaged form two-finger cursor 210, an engaged form one-finger swipe cursor 216, an engaged form two-finger swipe cursor 222, an engaged form one-finger press cursor 228, an engaged form two-finger press cursor 234, an engaged form one-finger press-and-hold cursor 240, an engaged form two-finger press-and-hold cursor 246, an engaged form pinch in cursor 252, and an engaged form pinch out cursor 258.

An engaged form cursor 204 through 258 may provide positive confirmation that the input that the user is entering corresponds with the input that was anticipated. Thus, the user would be prompted for a type of input by displaying a graphical cursor associated with that input, such as one of the base form cursors 102 through 156 shown in FIG. 1. If the user then enters the input associated with that displayed graphical cursor—if the detected input matches the anticipated input—an engaged form cursor 204 through 258 may be displayed to the user, so as to provide positive (and in this example, visual) confirmation that the user is entering the expected input.

From the user's point of view, the user would see a base form cursor 102 through 156 and would begin to enter the type of input associated with that base form cursor 102 through 156. The user then would see that the base form cursor 102 through 156 has changed to (or been replaced by) the engaged form of that cursor 204 through 258. Having seen that the engaged form of the cursor 204 through 258 is present, the user may visually confirm that he or she is entering the "correct" (or at least an anticipated) type of input.

The comments made above with regard to the appearance of various base form cursors and the similarities or differences in appearance between base form cursors also apply to the engaged form cursors 204 through 258 shown in FIG. 2. To briefly recap, the particulars of the appearance of engaged form cursors 204 through 258 may vary considerably from one embodiment to another, and although similarities not prohibited and may be useful for certain embodiments such similarities also are not required.

In addition, it is noted that although in the particular examples of FIG. 1 and FIG. 2 the base form cursors 102 through 156 and engaged form cursors 204 through 258 therein are graphically similar (though still distinct), this also is an example and is not required. It may be useful in at least some embodiments if engaged forms of cursors do resemble base forms of those cursors, for example, to provide continuity, for ease of user recognition, etc., but other arrangements may be equally suitable.

In particular, though the arrangements in FIG. 1 and FIG. 2 show engaged form cursors 204 through 258 that are "filled in" but otherwise similar to base form cursors 102 through 156, this is an example only. Base form cursors 102 through 156 may be filled in while engaged form cursors 204 through 258 are hollow, instead. Base forms of cursors and engaged forms of cursors also may vary in other ways, such as by color, through other difference in shape, through animation (e.g. the engaged form is animated while the base form is not), through transparency/opacity (e.g. the engaged form is transparent while the base form is opaque), etc.

Figure 3:
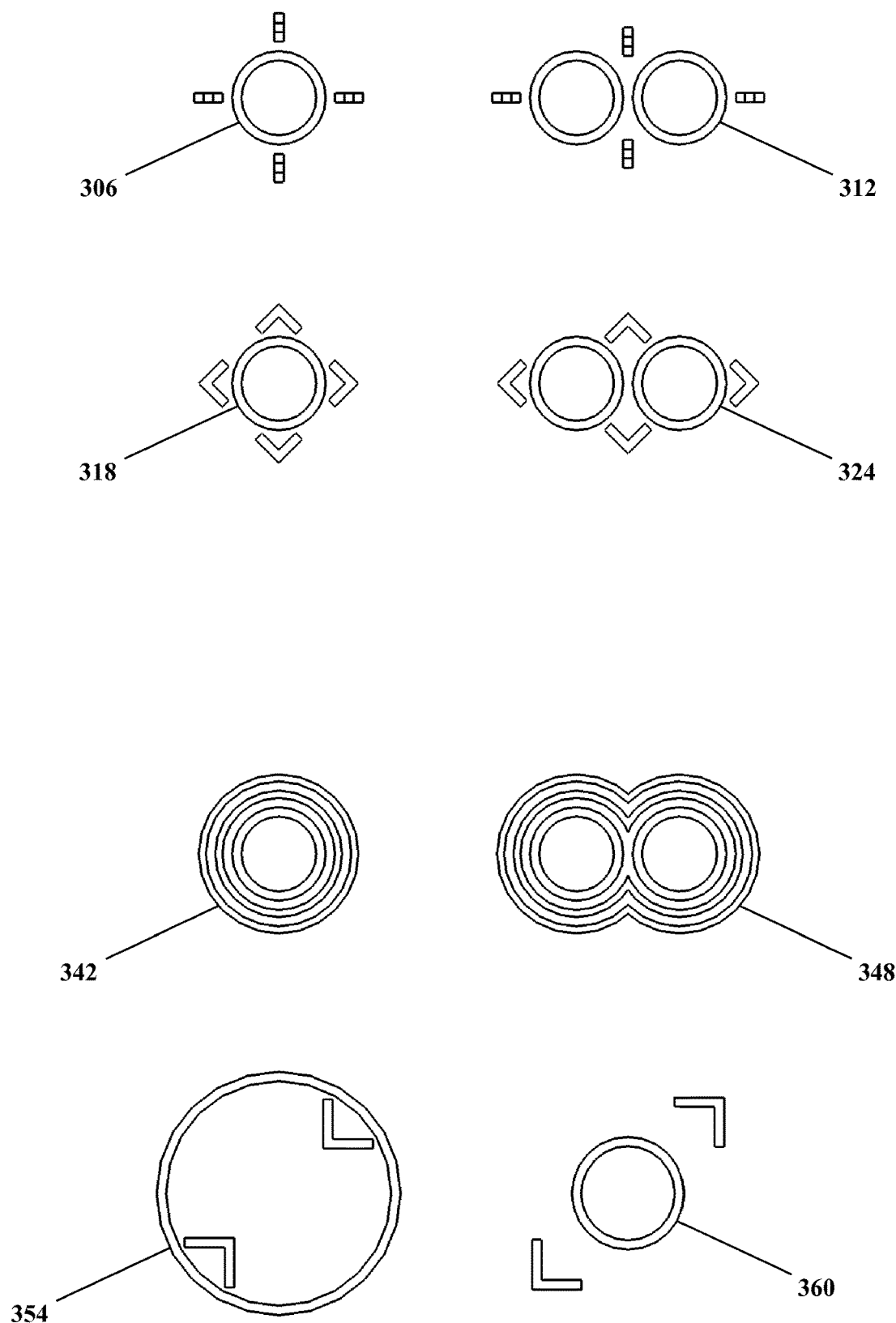
FIG. 3 shows example cursors for providing feedback regarding various inputs being hovered, in graphical form.

Other cursor forms also may be suitable, in addition to or in place of the base and engaged. With reference now to FIG. 3, therein is shown examples of hover forms of cursors 306 through 360. A hover form 306 through 360 of a cursor may be displayed for example when a user appears to be about to initiate an input. Thus, even before the user begins input, confirmation may be communicated to the user (e.g. by displaying hover form cursors 306 through 360) that the input he or she is preparing to enter is the anticipated input.

The term "hover" refers to a notion from two-dimensional digital desktops, wherein moving a cursor over some object on the desktop may cause some action related to the desktop object to take place. An alternative term may be "mouse-over". For example, hovering over an image file may cause the image size, format, creation date, etc. to be displayed.

However, as the term "hover" is used herein, hovering is not necessarily limited only to aligning a cursor with an object on a two-dimensional desktop. Rather, hover also may refer to preparing to enter input. For example, if a user were to enter a two-finger swipe in free space, for example as a gestural input for a head-mounted display, typically (though not necessarily) the user may move his or her hand toward a starting position for the swipe, may extend two fingers in preparation for entering the two-finger swipe, etc. Thus it may be possible to determine with at least some degree of reliability what the user is about to do, at least for certain inputs and/or certain embodiments.

Hover forms of cursors 306 through 360 are not required, however, nor is the ability to anticipate an input required (even if hover forms are present).

The cursors 306 through 358 include a hover form one-finger cursor 306, a hover form two-finger cursor 312, a hover form one-finger swipe cursor 318, a hover form two-finger swipe cursor 324, a hover form one-finger press-and-hold cursor 342, a hover form two-finger press-and-hold cursor 348, a hover form pinch in cursor 354, and a hover form pinch out cursor 360.

As may be seen, FIG. 3 does not show a hover form one-finger press cursor or a hover form two-finger press cursor. This is to emphasize that hover forms are not required (nor is any particular cursor form necessarily required), and to point out that even if certain cursors exhibit certain forms, not all cursors must include all such forms. That is, a one-finger swipe cursor may have base, engaged, and hover forms, while a one-finger press cursor may have only base and engaged forms.

The hover form cursors 306 through 360 are graphically similar to the base form cursors 102 through 156 (though still graphically distinct), though the hover form cursors 306 through 360 in FIG. 3 may be described as "compacted". For example the hover forms of the one-finger and two-finger cursors 306 and 312 in FIG. 3 include dashed crosshairs similar to the base forms of the one-finger and two-finger cursors 102 and 108 in FIG. 1, but drawn inward towards the respective centers. Likewise, the arrows in the hover form one-finger and two-finger swipe cursors 318 and 324 are drawn in; only two concentric rings/partial rings are present in the hover form one-finger and two-finger press-and-hold cursors 342 and 348; and the circles in the hover form pinch in and pinch out cursors 354 and 360 are shrunken and no longer dashed compared to FIG. 1.

Again, hover form cursors are not limited only to the arrangements shown in FIG. 3, nor to being compacted compared with base form cursors, nor even to sharing a similar variation (compacted or otherwise) compared with base form cursors.

As noted previously graphical indication of information may, to at least some extent, be arbitrary. FIG. 3 may provide an example thereof, at least in that a hover and compaction are not necessarily graphically related. However, if a user is made aware that for a given cursor suite compaction is used to indicate hover forms, then such an approach may be considered to be a graphical indication of the hover form even if no absolute relationship between compaction of cursors and hovering exists.

Figure 4:
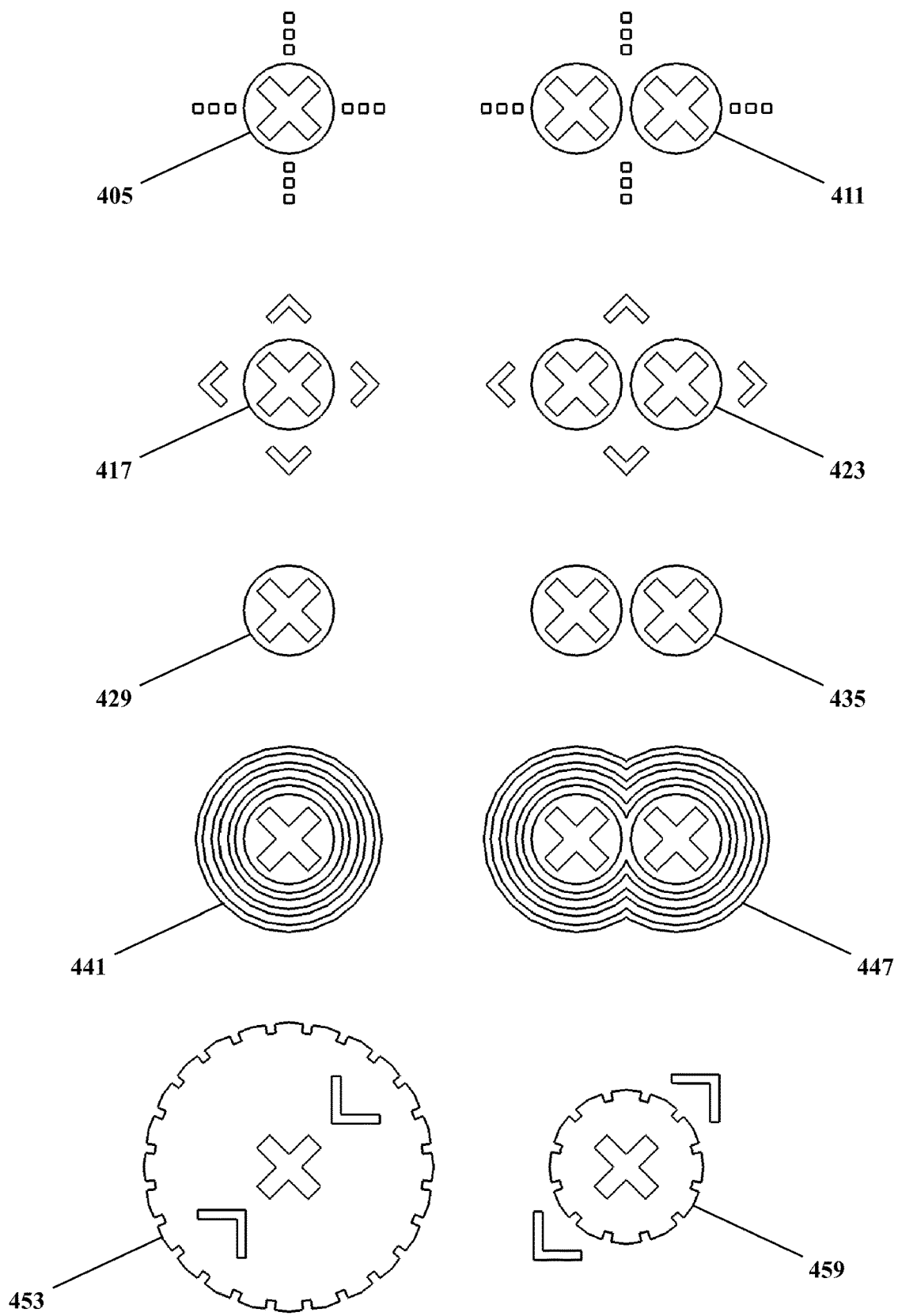
FIG. 4 shows example cursors for providing feedback regarding various error inputs, in graphical form.

Moving on to FIG. 4, yet another example set of cursor forms is shown. In FIG. 4, error forms 405 through 459 are shown. An error form 405 through 459 of a cursor may be displayed for example when a user has entered some form of input that does not match anticipated input. For example, if a user has been prompted to enter a pinch in input (e.g. by displaying the pinch in base cursor 150 in FIG. 1), but instead enters a two-finger swipe input, then the error form of the pinch in cursor 453 may be displayed (although the error form of the two-finger swipe input 423, or some generic error form, etc. might be displayed in addition and/or instead). The user thus may be provided with corrective feedback indicating that the user's input does not match what is anticipated.

The cursors 405 through 459 include an error form one-finger cursor 405, an error form two-finger cursor 411, an error form one-finger swipe cursor 417, an error form two-finger swipe cursor 423, an error form one-finger press cursor 429, an error form two-finger press cursor 435, an error form one-finger press-and-hold cursor 441, an error form two-finger press-and-hold cursor 447, an error form pinch in cursor 453, and an error form pinch out cursor 459.

The error form cursors 405 through 459 in FIG. 4 are graphically similar to the base form cursors 102 through 156 in FIG. 1 (though still graphically distinct), but the error form cursors 405 through 459 are filled in and include "X" markings in the circles thereof. Such "X" markings may graphically indicate to the user an error in input.

As previously noted, not all cursors necessarily will include an error form (or any other particular form). In addition, even when cursors do include error forms, not every mismatch between anticipated user input and detected user input necessarily will be an error, nor will the error form necessarily be displayed in such case. For example, in at least some instances multiple forms of input may be acceptable.

As a more concrete example, a photo viewing program may accept two-finger swipes to change from one photo to another, and pinches in and pinches out to zoom on the current photo. The anticipated input may be a two-finger swipe, and a base form of a two-finger swipe cursor (e.g. 126 in FIG. 1) may be displayed to the user. However, if the user applies a pinch in, the cursor may not display an error form, but may instead display an engaged form of a pinch in cursor (e.g. 252 in FIG. 2); the detected input of pinch in may be a valid input, and so may be confirmed as a valid input through displaying an engaged form of a corresponding cursor associated with that valid input, rather than an error form of the cursor associated with the anticipated input.

In more colloquial terms, if an input is not an error (even if the input was not expected), valid engaged cursor forms may be shown rather than the error form of the cursor for the expected input.

Figure 5:
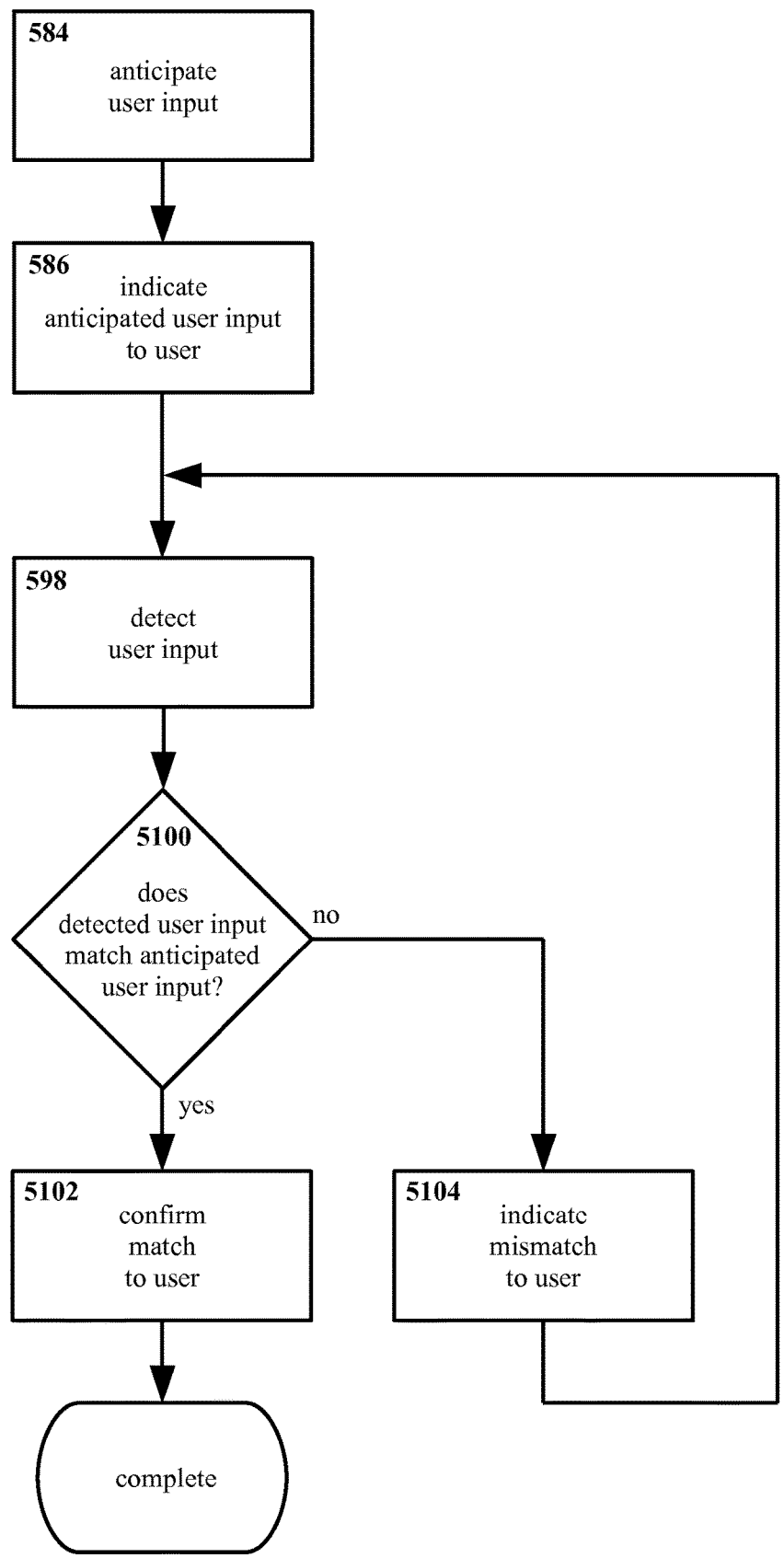
FIG. 5 shows an example method for interface control with prompt and feedback, in flow chart form.

Turning now to FIG. 5, at this point, it may be illuminating to describe in broad terms an example of how various cursors and forms thereof may be applied. More detailed examples are presented subsequently herein.

In FIG. 5, a user input is anticipated 584.

The "target" of the user input may vary considerably and is not limited. User input may be entered to some apparatus, system, etc., examples including but not limited to a desktop computer, a laptop computer, a portable electronic device such as a smartphone, a wearable electronic device such as a head mounted display, and so forth.

The type of user input also is not limited. User input may include but is not limited to gesture inputs, such as free space gesture inputs in three dimensions as may be used to control a head-mounted display or similar apparatus.

Further, the manner by which user input is anticipated is not limited. Typically though not necessarily, user input may be anticipated in that some specific type of input is needed at a given time and place, and it is then expected that if the input is entered the input will be of the type needed. As a more concrete example, if a head-mounted display is showing a 3D model of a heart for examination from different perspectives by a user, and the head mounted display is configured such that the 3D model of a heart rotates in response to one-finger free space swipes entered by the user, it may be anticipated that one-finger free space swipes may be so entered. Thus one-finger free space swipes may in such instance be considered an anticipated user input.

Continuing in FIG. 5, the anticipated user input is indicated 586 to the user. Such indication may be graphical, for example through displaying a cursor that is associated with the anticipated user input. To continue the example above regarding a 3D model of a heart, if one-finger free space swipes are anticipated as input, a base form of a one-finger swipe cursor 114 as shown in FIG. 1 may be displayed to the user via the head-mounted display.

User input is detected 598. The manner by which user input is detected is not limited. Typically though not necessarily, some sensor may detect the input. For example, again considering the example above, the head-mounted display may include a depth sensor, depth camera, RGB camera, stereo pair of RGB cameras, etc. so as to detect hand gestures executed by a user in free space. However other arrangements may be equally suitable.

A determination is made 5100 as to whether the detected user input matches the anticipated user input. If the determination 5100 is positive—if the detected user input does match the anticipated user input—then the method continues with step 5102. If the determination 5100 is negative—if the detected user input does not match the anticipated user input—then the method continues with step 5104.

If the determination 5100 is positive, then the match between the detected user input and the anticipated user input is confirmed 5102 to the user. For example, the cursor as displayed in the example of the 3D heart model may switch from the base form of a one-finger swipe cursor 114 as in FIG. 1 to the engaged form of the one finger swipe cursor 216 as in FIG. 2, providing a visual confirmation of the match to the user.

Following step 5102 the example method as illustrated in FIG. 5 is complete. However, it is noted that additional steps, including but not limited to repetitions of steps as shown, may be performed in at least certain embodiments.

However, if the determination 5100 is negative, then the mismatch between the detected user input and the anticipated user input is indicated 5104 to the user. For example, the cursor as displayed in the example of the 3D heart model may switch from the base form of a one-finger swipe cursor 114 as in FIG. 1 to the error form of the one finger swipe cursor 417 as in FIG. 2. Alternately, the cursor may remain in the base form of the one-finger swipe cursor 114 as in FIG. 1, without changing to the engaged form of the one finger swipe cursor 216 as in FIG. 2; in such case indication of the mismatch may be considered a negative indication, that is, rather than positively advising the user that the wrong input (or at least an unexpected input) is being entered, confirmation that the user is entering the anticipated input may be withheld. Positive and/or negative indications may be suitable for various embodiments.

The method then returns to step 598, again detecting user input. Thus for the example of FIG. 5, detected input is not positively confirmed as correct until and unless the input matches the anticipated input.

It is noted that outputting an indication of mismatch 5104 to the user does not necessarily imply that the user has entered incorrect or unexpected input. A mismatch between detected input and anticipated input also may occur if the detected input was incorrectly identified as some other input, if the detected input could not be identified, etc. Certain embodiments may distinguish between such possibilities or other possibilities.

For example, certain forms of input including but not limited to gestural input may be subject to what might be referred to as "degeneration". Consider a two-finger hand gesture swipe input that is defined so as to be entered with the index and middle finger of one hand fully extended and held adjacent one another, with a horizontal motion of the fingertips. Depending on precisely how the gesture is detected and/or identified, even if some degree of finger separation, bends in the knuckles, curve or misdirection in the motion path, etc. is present the gesture may still be recognized. However, at some point, the actual gesture made by a user may differ so much from the defined gesture that the actual gesture may no longer be recognizable. It may be said that the hand gesture is too "degenerate" to be recognized.

In such instance, the user may have chosen the proper input—that is, the user intended to enter a "proper" two-finger swipe—but nevertheless may not actually have entered a two-finger swipe—that is, the hand motion that the user made was not recognizable as a two-finger swipe within the definition thereof. Regardless of whether the user thinks he or she entered the "correct" gesture, the gesture was not recognized.

In certain embodiments, a case wherein an input is not recognizable as a gesture may be treated differently than a case wherein a recognizable but incorrect gesture is detected. Both situations (gesture not recognized, gesture recognized but incorrect) may in some sense be errors, but it may be useful to distinguish between "input not recognized" and "input incorrect" (or "input not as anticipated"). Thus, embodiments may have multiple forms that may be considered as error forms, for example, an "incorrect input" form, an "input not recognized" form, a "system malfunction" form, etc.

It is also noted that not all embodiments necessarily will include both a confirmation of match 5102 and an indication of mismatch 5104. In certain embodiments, a match may not be confirmed (e.g. no engaged form cursor may be displayed) but a mismatch may be indicated (e.g. with an error form cursor), or vice versa. While embodiments that confirm a match and indicate a mismatch are not prohibited, not all embodiments are required both to confirm the match and indicate a mismatch.

In sum, in the arrangement of FIG. 5 the user is presented with an indication of what input(s) are expected for a given situation (for example by displaying a graphical cursor indicative of the expected input(s)), the user input is detected, and the user is provided with a confirmation that the input is as expected and/or an indication that the input is not as expected.

Now with reference to FIG. 6A through FIG. 6D, another example method is provided, this example referring more particularly to individual cursor forms such as those previously shown and described with regard to FIG. 1 through FIG. 4.

Figure 6A:
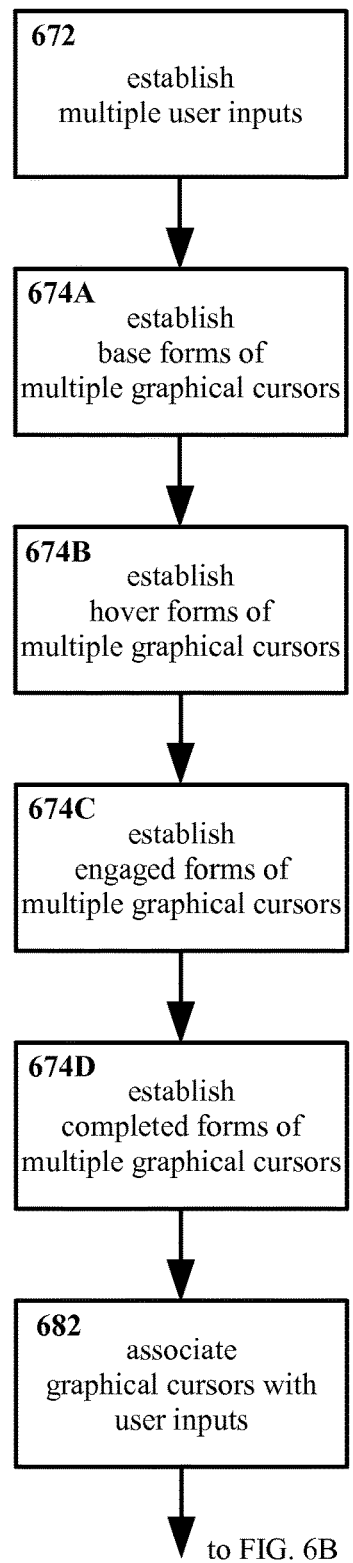
FIG. 6A through FIG. 6D show another example method for interface control with prompt and feedback, referring to example cursors, in flow chart form.

In FIG. 6A, multiple user inputs are established 672. The number of user inputs is not limited, although if only a single user input were established 672 then the question of distinguishing among different user inputs may be moot.

The term "establish" is used broadly herein. It is noted that to "establish" something may, depending on particulars, refer to either or both the creation of something new (e.g. establishing a business, wherein a new business is created) and the determination of a condition that already exists (e.g. establishing the whereabouts of a person, wherein the location of a person who is already present at that location is discovered, received from another source, etc.). Similarly, establishing a user input may encompass several potential approaches, such as defining the input (e.g. through the use of executable instructions instantiated on a processor), obtaining the inputs and/or input definitions from a data store such as a hard drive or solid state drive, receiving the inputs and/or input definitions via communication with some external device, system, etc., and so forth. Other arrangements also may be equally suitable, and embodiments are not limited with regard to how either inputs or other actions and/or entities may be established.

In addition, the nature and/or function of the inputs is not limited. As an example, inputs may define hand gestures performed in free space, and/or sensor data indicating that such inputs have been performed, along with actions to be taken in response to such gestures. As a more concrete example, inputs may include a two-finger swipe in free space as detected by a depth camera and an RGB camera on a head-mounted display, which is associated with a processor instruction to rotate a 3D model being displayed. However, this is an example only, and many other inputs may be suitable.

Continuing in FIG. 6A, base forms of multiple graphical cursors are established 674A. The number of graphical cursors also is not limited, although again if only a single graphical cursor were established 672A then the question of distinguishing among different user inputs may be moot. In addition, typically though not necessarily, the number of graphical cursors may be less than or equal to the number of inputs established 672. That is, while a single cursor may be associated with more than one input (e.g. one cursor for all two-finger swipes regardless of what direction(s) those swipes are in, or one cursor for all swipes regardless of the number of fingers, etc.), typically a given input may be associated with no more than one cursor.

Hover forms of multiple graphical cursors are established 674B. Engaged forms of multiple graphical cursors are established 674C. Completed forms of multiple graphical cursors are established 674D. Various examples of cursor forms have been shown and described with regard to FIG. 1 through FIG. 4, such as base forms, hover forms, and engaged forms. Completed forms have not been illustrated in FIG. 1 through FIG. 4, but may be understood as representing a further form of some cursor; for example, cursors similar to those shown in FIG. 2 but with a checkmark within the filled circle to indicate completion of an input, etc. Not all possible cursor forms are described herein; the number of forms of a cursor is not limited, nor are cursor forms limited only to those shown and described herein.

The graphical cursors are associated 682 with at least some of the user inputs. That is, one cursor (possibly in various forms such as base, engaged, etc.) may be associated with all two-finger swipe inputs, another cursor may be associated with pinch in inputs, and so forth. The manner of association is not limited. Typically though not necessarily, the association may be implemented through executable instructions instantiated on a processor, for example by "tagging" each input definition as being associated with a cursor, and/or vice versa. Other arrangements may be equally suitable.

Figure 6B:
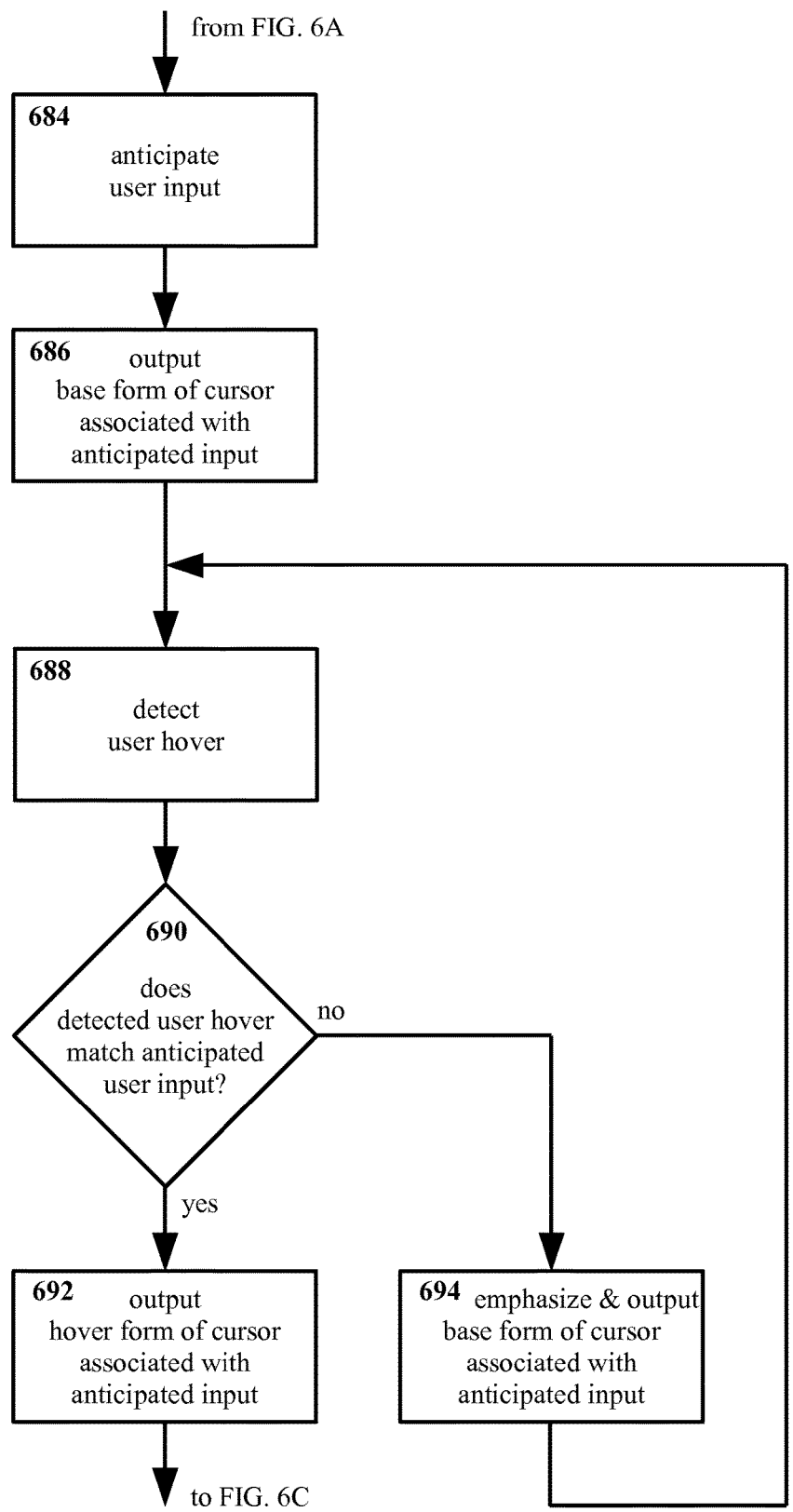

Continuing in FIG. 6B, user input is anticipated 684. The base form of the cursor associated with that anticipated input is then outputted 686, for example to a graphical display so as to be viewable by a user. Through outputting 686 the graphical cursor associated with the anticipated input, the user may be advised of the type(s) of input that are expected in a given situation.

In some conditions, two or more different inputs potentially associated with two or more different cursors may be suitable. In such instances, some determination may be made as to which of the suitable inputs is most likely, and the base form of the cursor associated with that input outputted 686. Alternately, one of the suitable inputs may be selected at random, and the base form of the cursor associated with that input outputted 686. As another alternative, if suitable inputs are associated with two or more cursors, the base forms of those cursors may be displayed together, or in sequence (e.g. visibly "cycling through" the several cursors), etc. Other arrangements also may be suitable.

The user hover is detected 688. As noted previously, detecting user hover (and the use of hover form cursors) may not be present in all embodiments, but is shown here as an example. If user hover is not determined, hover form cursors are not present, etc., then certain steps as shown in FIG. 6A through FIG. 6D also may not be present (or may be unnecessary); this may be true of other cursor forms as well for various embodiments not utilizing certain cursor forms. Conversely, embodiments using additional cursor forms may include steps addressing those additional cursor forms.

Still with reference to FIG. 6B, a determination is made 690 as to whether the detected user hover matches the anticipated user input. That is, does the input that the user appears to be "about to do" correspond with the input that is anticipated? If the determination 690 is positive—if the detected user hover matches the anticipated user input—then the method continues with step 692. If the determination 690 is negative—if the detected user hover does not match the anticipated user input—then the method continues with step 694.

If the determination 690 is positive, the hover form of the cursor associated with the anticipated input is outputted 692, for example to a graphical display. Through outputting 692 the hover form of the graphical cursor that is associated with a hover that matches the anticipated input, the user may receive confirmation that the input he or she is about to enter (or is detected as being about to enter) is suitable (or at least is as expected).

If the determination 690 is negative, the base form of the cursor associated with the anticipated input is emphasized and outputted 694, for example to a graphical display. Through emphasizing and outputting 694 the base form of the graphical cursor that is associated with a hover that matches the anticipated input, the user may be advised that the input he or she is about to enter (or is detected as being about to enter) may be unsuitable (or at least may be unexpected).

With regard to emphasizing the base form, emphasis may be applied in many ways. For certain embodiments, the base form may be enlarged. Alternately, the base form may be outputted with a different and/or more noticeable color, with a higher degree of opacity, while blinking or animated, etc. Emphasis also may include non-visual cues such as audible sounds (e.g. an "error beep"), etc. Emphasis may include text messages (e.g. "error", "incorrect input", "input not recognized", "input cannot be executed", etc.) in addition to or instead of graphical or other sensory signals. The type of emphasis is not limited and may vary considerably from one embodiment to another.

Emphasizing the base form and using an error form may to some degree overlap. For example, if the base form of a cursor is a shape displayed in white and the error form is the same shape displayed in red, then in practice this may be equivalent to emphasizing the base form by changing the base form's color to red. However, not all possible types of emphasis are necessarily similar to error forms, nor vice versa.

As shown in FIG. 6B, one the base form of the cursor has been emphasized and outputted 694, the method returns to again detecting the user hover 688. This may be suitable for certain embodiments, for example, so as to provide the user an opportunity to adjust his or her hover (e.g. change the input they are about to give). However, such a loop is not required, and in certain embodiments it may be suitable to output 694 the emphasized base form of the cursor and move on (in the example of FIG. 6A through FIG. 6D, this may correspond with continuing to step 698 in FIG. 6C rather than returning to step 688 in FIG. 6B); this may represent the user being advised of the mismatch between hover and anticipated input, without necessarily requiring that the user adjust his or her hover.

Figure 6C:
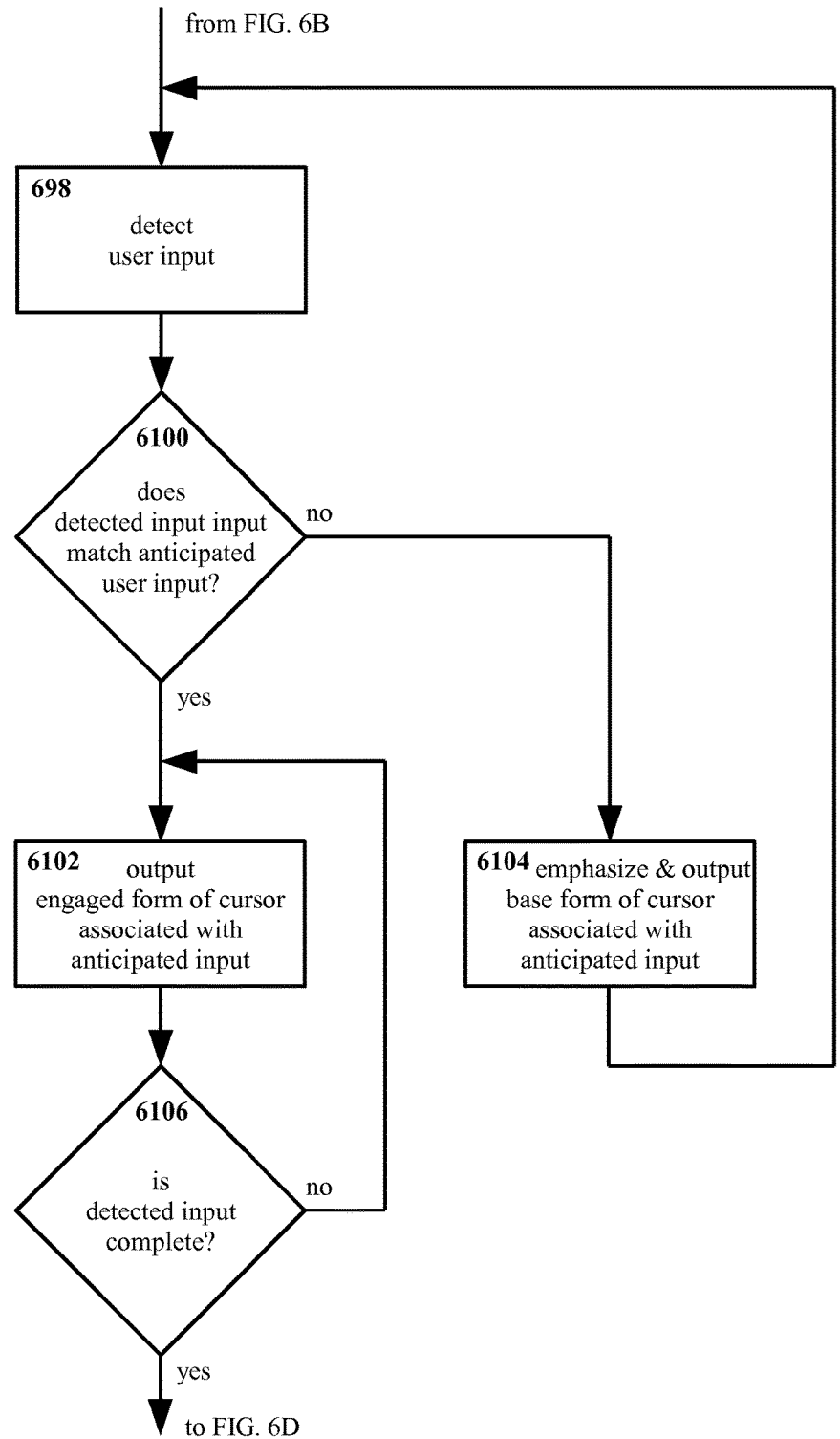

Now with reference to FIG. 6C, the user input is detected 698.

A determination is made 6100 as to whether the detected user input matches the anticipated user input. That is, does the input entered by the user (or at least initiated by the user) correspond with the input that is anticipated? If the determination 6100 is positive—if the detected user input matches the anticipated user input—then the method continues with step 6102. If the determination 6100 is negative—if the detected user input does not match the anticipated user input—then the method continues with step 6104.

If the determination 6100 is positive, the engaged form of the cursor associated with the anticipated input is outputted 6102, for example to a graphical display. Through outputting 6102 the engaged form of the graphical cursor that is associated with the anticipated input, the user may receive confirmation that the input he or she entering (or is detected as entering) is suitable (or at least is as expected).

If the determination 6100 is negative, the base form of the cursor associated with the anticipated input is emphasized and outputted 6104, for example to a graphical display. Through emphasizing and outputting 6104 the base form of the graphical cursor that is associated with the anticipated input, the user may be advised that the input he or she is entering (or is detected as entering) may be unsuitable (or at least may be unexpected).

The emphasis applied to the base form may vary, as noted above with regard to step 694. In addition, the emphasis applied to the base form in step 6104 may be the same as or similar to the emphasis applied to the base form in step 694 or may be different. For example, the emphasis in step 694 (based on hover mismatch) may be to turn the base form yellow, while the emphasis in step 6104 (based on input mismatch) may be to turn the base form red. Other arrangements also may be suitable.

Also as noted with regard to step 694, although in FIG. 6C the method is shown as returning to step 698 after step 6104, this is an example and other arrangements may be suitable. For example, even if the detected input does not match the anticipated input, the detected input may be accepted and executed (in the example of FIG. 6C, this may include proceeding with step 6106 rather than returning to step 698).

Still with reference to FIG. 6C, a determination is made 6106 as to whether the detected input is complete. For example, considering hand gestures the determination may be made 6106 by measuring the speed, position, orientation, etc. of a user's hand so as to see whether the hand has stopped, or has reached some state otherwise indicate that a gesture has been completed. However, other arrangements may be suitable.

If the determination 6106 is negative—if the detected input is incomplete (or at least is determined to be incomplete)—the method returns to step 6102 and the engaged form of the cursor continues to be output 6102. If the determination 6106 is positive—if the detected gesture is completed (or at least is determined to be complete)—the method continues in FIG. 6D.

Figure 6D:
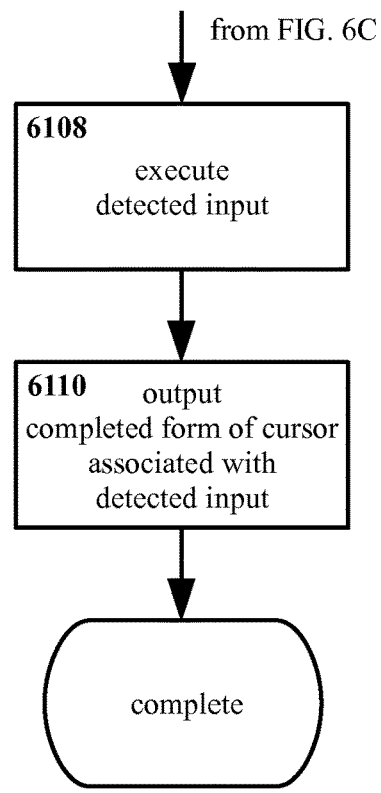

In FIG. 6D, the detected input is executed 6108. For example, if the input associated with a two-finger swipe is to rotate a 3D object, that 3D object is rotated.

It is noted that given the arrangement of FIG. 6A through FIG. 6D, the detected input also is the anticipated input. This may not necessarily be the case, however; as noted, in certain embodiments inputs other than anticipated inputs may be accepted, and in such case, the input that is detected and executed 6108 may be different from the input that is anticipated.

The completed form of the cursor associated with the detected input is output 6110. Again, it is noted that the detected input may be the same as the anticipated input for the arrangement in FIG. 6A through FIG. 6D, but this may not necessarily be true for all embodiments. Regardless, typically (though not necessarily) if an executed form is outputted 6110, the executed form will be of the cursor associated with the input that is in fact detected, rather than the executed form of the input that is anticipated. That is, a cursor form showing completion of the input actually detected may be outputted 6110, even if different from the input that was expected.

Alternately, if the completed detected input does not match the anticipated input, the error form of the cursor associated with the anticipated input and/or the error form of the cursor associated with the detected input may be outputted instead. That is if the input actually detected is different from what is expected, then an error form of a cursor may be outputted rather than a completed form.

Figure 7A:
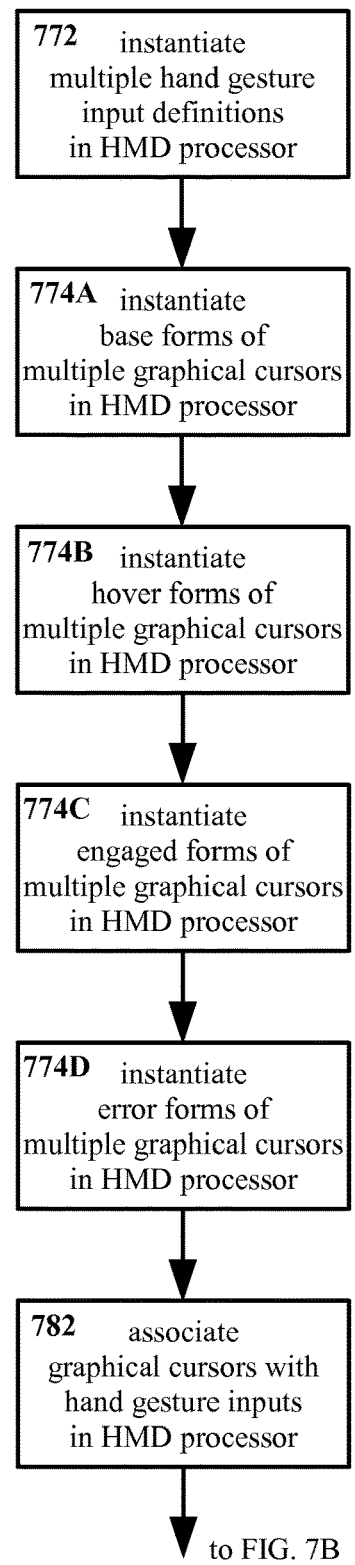
FIG. 7A through FIG. 7C show another example method for interface control with prompt and feedback, specific to the example of hand gesture inputs to a head-mounted display, in flow chart form.
Figure 7B:
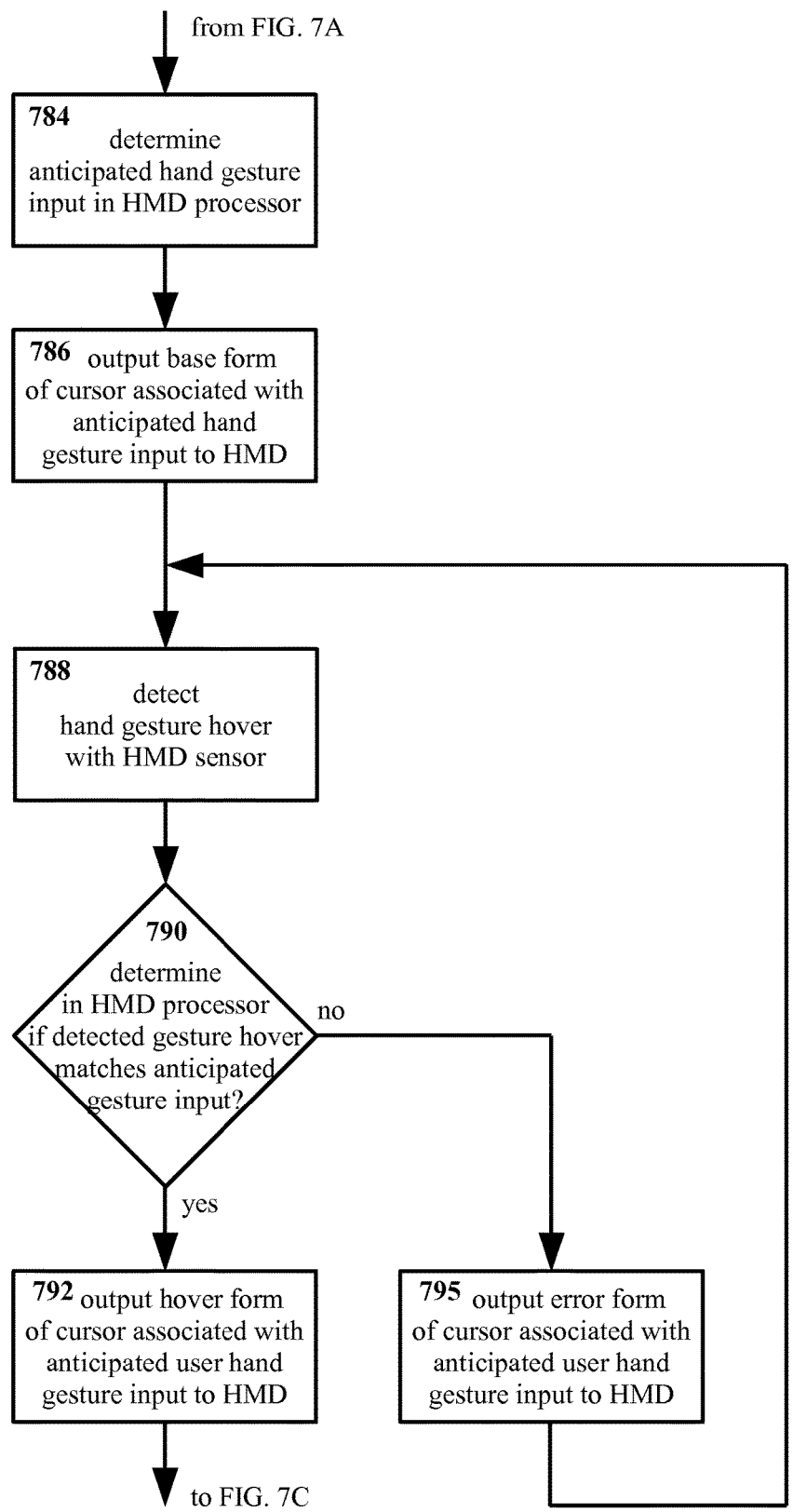
Figure 7C:
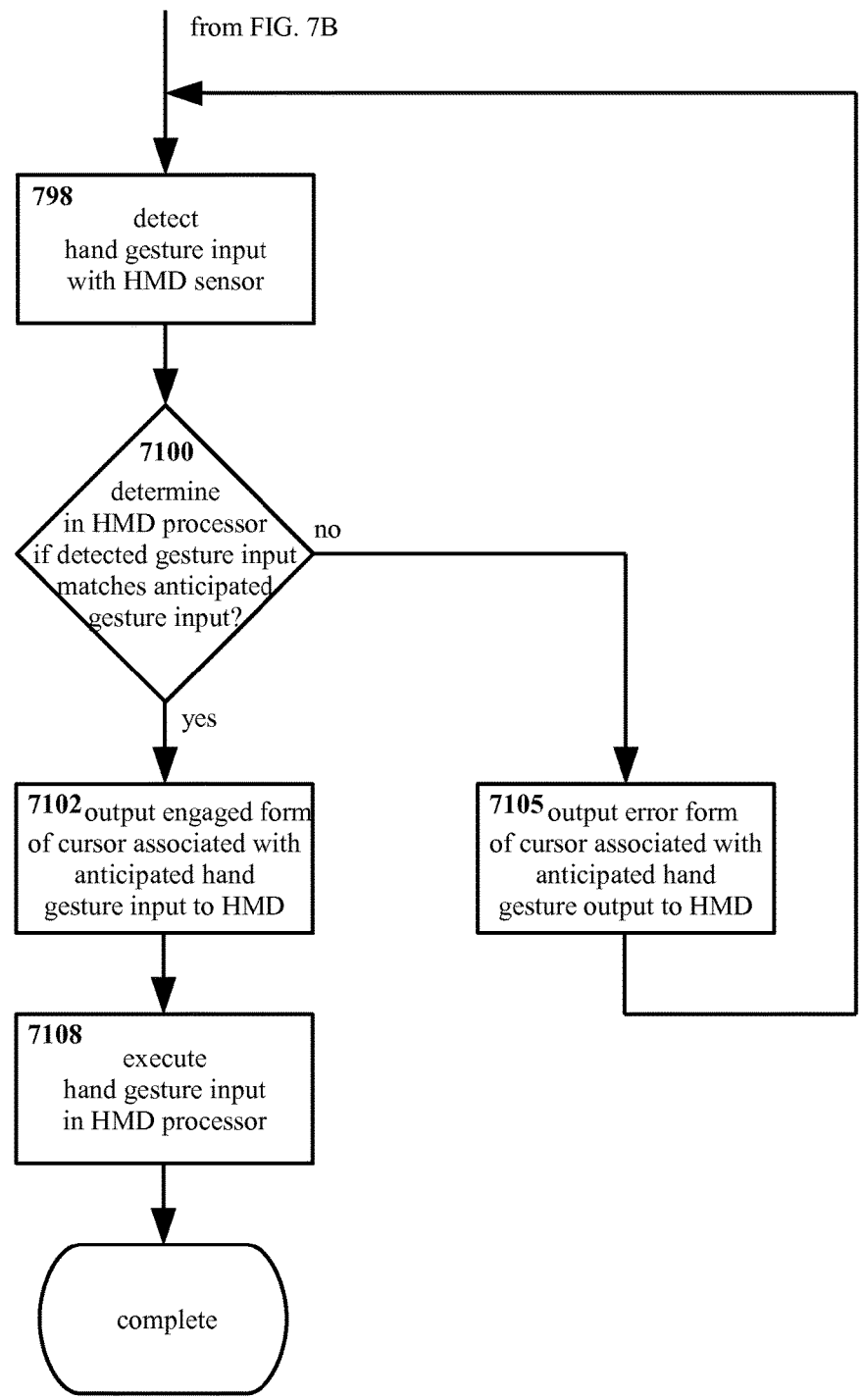

Now with reference to FIG. 7A through FIG. 7C, another example method is provided, this example referring more particularly to implementation with a head-mounted display (abbreviated "HMD" in places within FIG. 7A through FIG. 7C), with a processor disposed thereon.

In FIG. 7A, definitions for multiple hand gesture inputs are instantiated 772 onto the processor of a head mounted display. For example, one and/or two-finger swipes, presses, etc. as applied by a user's hand may be defined, along with some action, executable instruction, etc. that is to be carried out in response to those hand gestures.

Base forms multiple graphical cursors are instantiated 774A onto the head mounted display processor. For example, base forms for a one-finger general cursor 102, a two-finger general cursor 108, a one-finger swipe cursor 114, a two-finger swipe cursor 120, a one-finger press cursor 126, a two-finger press cursor 132, a one-finger press-and-hold cursor 138, a two-finger press-and-hold cursor 144, a pinch in cursor 150, and a pinch out cursor 156 as illustrated in FIG. 1 may be so instantiated; however, this is an example only and is not limiting.

Hover forms, engaged forms, and error forms of cursors also are instantiated 744B, 744C, and 744D onto the processor of the head-mounted display. Although four cursor forms are shown to be instantiated onto the head mounted display processor in FIG. 7A in steps 744A, 744B, 744C, and 744D, this is an example only. More or fewer cursor forms may be instantiated (or otherwise established), and as noted previously not all cursors necessarily will have all forms.

The graphical cursors are associated 782 with one or more of the hand gesture inputs in the head-mounted display processor.

Now with reference to FIG. 7B, the anticipated hand gesture input is determined 784 in the head-mounted display processor. For example, the hand gesture(s) that are acceptable and/or most likely to be entered by the user may be identified based on recent actions (e.g. what gestures the user has performed immediately beforehand), based on previous similar situations (e.g. what gestures the user has performed when using the same program or in the same environment), based on what functions the head mounted display is carrying out (e.g. the programs being run, the information being displayed, etc.), other contextual factors, and so forth.

The base form of the cursor associated with the anticipated hand gesture input is outputted 786 to the head mounted display. For example, the cursor may be displayed on near-eye displays, such that the user sees the cursor overlaid onto the physical environment (e.g. if the near-eye displays are see-through) or onto a virtual or augmented reality environment, etc. In such manner, the user may be prompted regarding anticipated gesture inputs.

Still with reference to FIG. 7B, a hover corresponding with a gesture input is detected 788 using information received from one or more sensors disposed on the head mounted display. For example, the head-mounted display may include a depth imager and an RGB imager, which together may provide sufficient information to detect and identify hand positions, motions, contextual factors, etc. within those sensors' fields of view as may correspond with a hover for some hand gesture input. Based for example on those hand position, motions, contextual factors, etc., a hover for a hand gesture input may be detected.

Detecting the hand gesture hover 788 also may include (but is not required to include) analysis within the processor, for example the processor may analyze the content of images obtained by the sensors, may apply algorithms to such images, or otherwise may determine that a hand gesture hover is taking place and/or identify which hand gesture hover is taking place.

A determination is made 790 in the head-mounted display processor as to whether the detected user hand gesture hover matches the anticipated user hand gesture input.

If the determination 790 is positive—if the detected user hand gesture hover matches the anticipated user hand gesture input—then the hover form of the cursor associated with the anticipated user hand gesture input is outputted 792 to the head mounted display.

If the determination 790 is negative—if the detected user hand gesture hover does not match the anticipated user hand gesture input—then the error form of the cursor associated with the anticipated user hand gesture input is outputted 795 to the head mounted display, and the method returns to step 788. It is noted that this arrangement differs somewhat from that in FIG. 6B as previously described; where in FIG. 6B the base form of the relevant cursor is emphasized, in FIG. 7B an error form is outputted 795.

Now with reference to FIG. 7C, a user hand gesture input is detected 798 using information received from one or more sensors disposed on the head mounted display. For example, the head-mounted display may include a depth imager and an RGB imager, which together may provide sufficient information to detect and identify hand positions, motions, contextual factors, etc. within those sensors' fields of view as may correspond with a hand gesture input.

As with the hand gesture hover in step 788, detecting the hand gesture input 798 also may include (but is not required to include) analysis within the processor.

A determination is made 7100 in the head-mounted display processor as to whether the detected user hand gesture input matches the anticipated user hand gesture input.

If the determination 7100 is positive—if the detected user hand gesture input matches the anticipated user hand gesture input—then the engaged form of the cursor associated with the anticipated user hand gesture input is outputted 7102 to the head mounted display.

If the determination 7100 is negative—if the detected user hand gesture input does not match the anticipated user hand gesture input—then the error form of the cursor associated with the anticipated user hand gesture input is outputted 7105 to the head mounted display, and the method returns to step 798. As noted with regard to step 795, it is noted that this arrangement differs somewhat from that in FIG. 6C as previously described; where in FIG. 6C the base form of the relevant cursor is emphasized, in FIG. 7B an error form is outputted 7105.

Continuing in FIG. 7C, the hand gesture input is executed 7108 in the head-mounted display processor. Although not specified in FIG. 6D, execution 7108 of the detected hand gesture input may include (but is not required to include) entities other than the processor, and/or other than the head-mounted display. For example, if the hand gesture input associated with a two-finger swipe is to rotate a 3D object, that 3D object is rotated; rotation of the 3D object may be outputted from the display(s) of the head mounted display, may be outputted from other screens in communication with the head mounted display, may be logged internally in a data store or transmitted externally to some other device or system, etc.

It is emphasized that the arrangement is shown in FIG. 7A through FIG. 7C is an example only, particular to a head-mounted display utilizing hand gesture inputs. Embodiments are not limited only to the arrangement shown in FIG. 7A through FIG. 7C, and may vary considerably.

Figure 8:
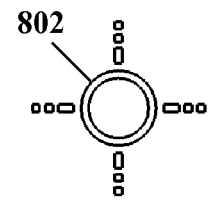
FIG. 8 shows an example suite of graphical cursors for an example interface, in graphical form.
Figure 8:
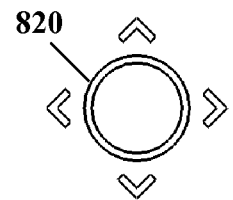
Figure 8:
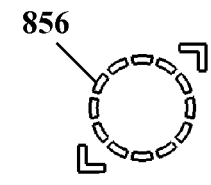
Figure 8:
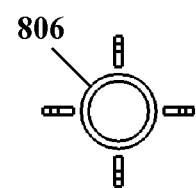
Figure 8:
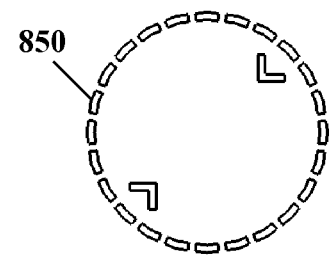
Figure 8:
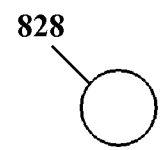
Figure 8:
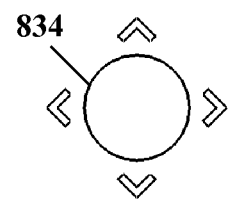
Figure 8:
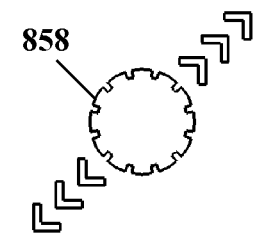
Figure 8:
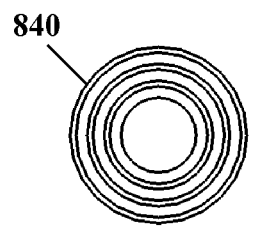
Figure 8:
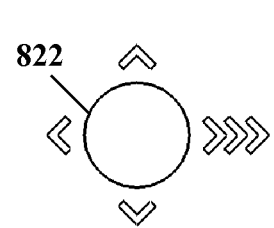
Figure 8:
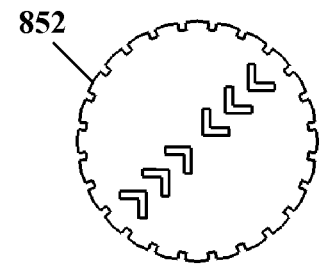

Now with reference to FIG. 8, therein is shown an example of a suite of cursors and forms thereof. Such a suite may represent the entire arrangement of visible cursors/forms for a particular embodiment. For example, a head mounted display may use all of the cursors and forms are shown, and no others. The arrangement is shown in FIG. 8 thus would include cursors and/or forms for all of the functions performed in some particular embodiment, such as an interface for a head-mounted display, a mobile operating system, etc. It is noted that the FIG. 8 does not include all of the cursors referred to elsewhere herein, nor all of the forms and that the distribution of cursors and forms is not comprehensive even for those shown (for example, hover forms are shown for some cursors but not for all, etc.). Comprehensive or uniform arrangements of cursors and forms are not required for all embodiments, as may be seen from FIG. 8. In addition, it is emphasized that the arrangement shown in FIG. 8 is an example only, and is not limiting.

In addition, where certain previous examples have shown a simple one-to-one arrangement of forms for a cursor—that is, one base form, one hold form, one engaged form, etc.—as shown in FIG. 8 cursor/form arrangements are not required to be one-to-one. A single cursor may have more than one of a given type of form (e.g. two engaged forms).

In FIG. 8, a base form of a one-finger cursor 802 is shown. A base form one-finger cursor 802 as shown may serve as a default, wherein specific inputs or types of inputs may not be called for, or wherein several different inputs may be suitable. Alternately, the base form one-finger cursor 802 may serve to represent one-finger inputs only, for example, if one-finger gestures are used for certain inputs (e.g. press inputs, press-and-hold inputs, etc.) while two-finger gestures are used for other inputs (e.g. swipes, pinches, etc.). Given the distinctive appearance shown for the base form one-finger cursor 802, displaying the base form one-finger cursor 802 may prompt a user to enter a one-finger input.

A hover form of the one-finger cursor 806 also is shown in FIG. 8. As may be seen, the hover form of the one-finger cursor 806 is graphically similar to but distinct from the base form one-finger cursor 802. In displaying the hover form of the one-finger cursor 806 in response to a user hover, the user may be given graphical confirmation that the user hover has been detected (and thus for example that the system "recognizes" the user's action in hovering over the cursor).

No engaged form for a general one-finger cursor is shown in FIG. 8. However, an engaged form one-finger press cursor 828 also is shown, along with an engaged form one-finger press-and-hold cursor 840. In certain embodiments, it may be suitable for engaged forms to be specific to particular inputs and/or actions, even if the corresponding base form is general. Thus, the engaged form one-finger press cursor 828 and engaged form one-finger press-and-hold cursor 840 may serve as engaged forms of the base form one-finger press cursor 828 for the particular example arrangement shown in FIG. 8.

Given such an arrangement, a base form one-finger cursor 802 may be displayed when that cursor is neither engaged nor hovered and the hover form one-finger cursor 806 displayed when the cursor is hovered. Then, either the engaged form one-finger press cursor 828 or the engaged form one-finger press-and-hold cursor 840 may be displayed when the cursor is engaged, depending on whether the user inputs a press or a press-and-hold. (At least potentially, the engaged form one-finger press cursor 828 may be shown first in response to a press, and the engaged form one-finger press-and-hold cursor 840 shown after the press has been held for some period.)

In some sense then, the four elements 802, 806, 828, and 840 all may be considered forms of a single cursor, with a base form 802, a hover form 806, and two different engaged forms 828 and 840. Although for simplicity certain cursors are shown and described herein with a simple, linear relationship of forms—e.g. one base form, one hover form, one engaged form—as may be seen from FIG. 8 embodiments are not limited only thereto. A single cursor may include multiple forms for each of several states, as elements 828 and 840 in FIG. 8 both may be considered to be engaged forms for a one-finger cursor.

Considering elements 802, 806, 828, and 840 collectively, the base form one-finger cursor 802 may be displayed to prompt a user for a one-finger gesture input, the hold form one-finger cursor 806 may be displayed to confirm to the user that a one-finger gesture hover has been detected, and the engaged form one-finger press cursor 828 or the engaged form one-finger press-and-hold cursor 840 displayed to confirm to the user that a one-finger press gesture or one-finger press-and-hold gesture respectively has been detected.

FIG. 8 also shows a base form two-finger cursor 820.

A base form two-finger cursor 820 may serve as a default if specific inputs or types of inputs may be called for, or several different inputs may be suitable. Alternately, the base form two-finger cursor 820 may represent two-finger inputs only (e.g. as distinct from one-finger inputs). Given the distinctive appearance shown for the base form two-finger cursor 820, displaying the base form two-finger cursor 820 may prompt a user to enter a two-finger input.

No hover form of a two-finger cursor is shown in FIG. 8. Given such an arrangement, it may be that the base form two-finger cursor 820 is displayed even if a hover is detected, or that no hover is detected or considered, etc. Thus to a viewer, the base form two-finger cursor 820 may not visibly change in response to a hover (though in other embodiments a hover form may be included and displayed).

As with the on-finger cursors, two different engaged form two-finger cursors are shown: an engaged form two-finger press cursor 834 and an engaged form two-finger swipe cursor 822. The engaged form two-finger press cursor 834 may be displayed to the user in response to the user entering (or at least beginning to enter) a two-finger press input, while the engaged form two-finger swipe cursor 822 may be displayed to the user in response to the user entering (or at least beginning to enter) a two-finger swipe input. Thus, display of element 834 or 822 may serve to graphically confirm to the user that a two-finger press input or two-finger swipe input has been detected.

Still, with reference to FIG. 8, a base form pinch out cursor 856 is shown along with an engaged form pinch out cursor 858. No hover form is shown. The base form pinch out cursor 856 may be displayed to prompt a user to enter a pinch out input, while the engaged form pinch out cursor 858 may be displayed to confirm to a user that a pinch out input has been detected.

A base form pinch in cursor 850 also is shown along with an engaged form pinch in cursor 852, again with no hover form shown. The base form pinch in cursor 850 may be displayed to prompt a user to enter a pinch in input, while the engaged form pinch in cursor 852 may be displayed to confirm to a user that a pinch in input has been detected.

Thus the arrangement shown in FIG. 8 may be considered as four cursors: a one-finger cursor 802, 806, 828, and 840, a two-finger cursor 820, 834, and 822, a pinch in cursor 856 and 858, and a pinch out cursor 850 and 852. Where the one-finger cursor includes one base form 802, one hover form 806, and two engaged forms 828 and 840, the two-finger cursor includes a base form 820 and two engaged forms 834 and 822 but no hold form, and the pinch in cursor includes only a base form 856 and an engaged form 858, with the pinch out cursor likewise including only a base form 850 and an engaged form 852. Such arrangements, or other arrangements without one-to-one correspondence between forms for various cursors, may be suitable for certain embodiments (though one-to-one correspondence also is not prohibited).

As noted, certain cursors may have more than one form of a given type, for example having two engaged forms, while certain cursors also may lack any forms of a given type, for example having no hover form. Conversely, certain cursor forms may be common to more than one cursor. For example, several cursors may share a common error form, or a single common completed form (although no error forms or completed forms are shown in the example of FIG. 8); in such instance, some or all error forms output may look similar or identical, regardless of what cursor is displayed. Such an arrangement may serve to communicate to a user that the input is incorrect (or at least unexpected), without necessarily specifying a particular error.

Figure 9:
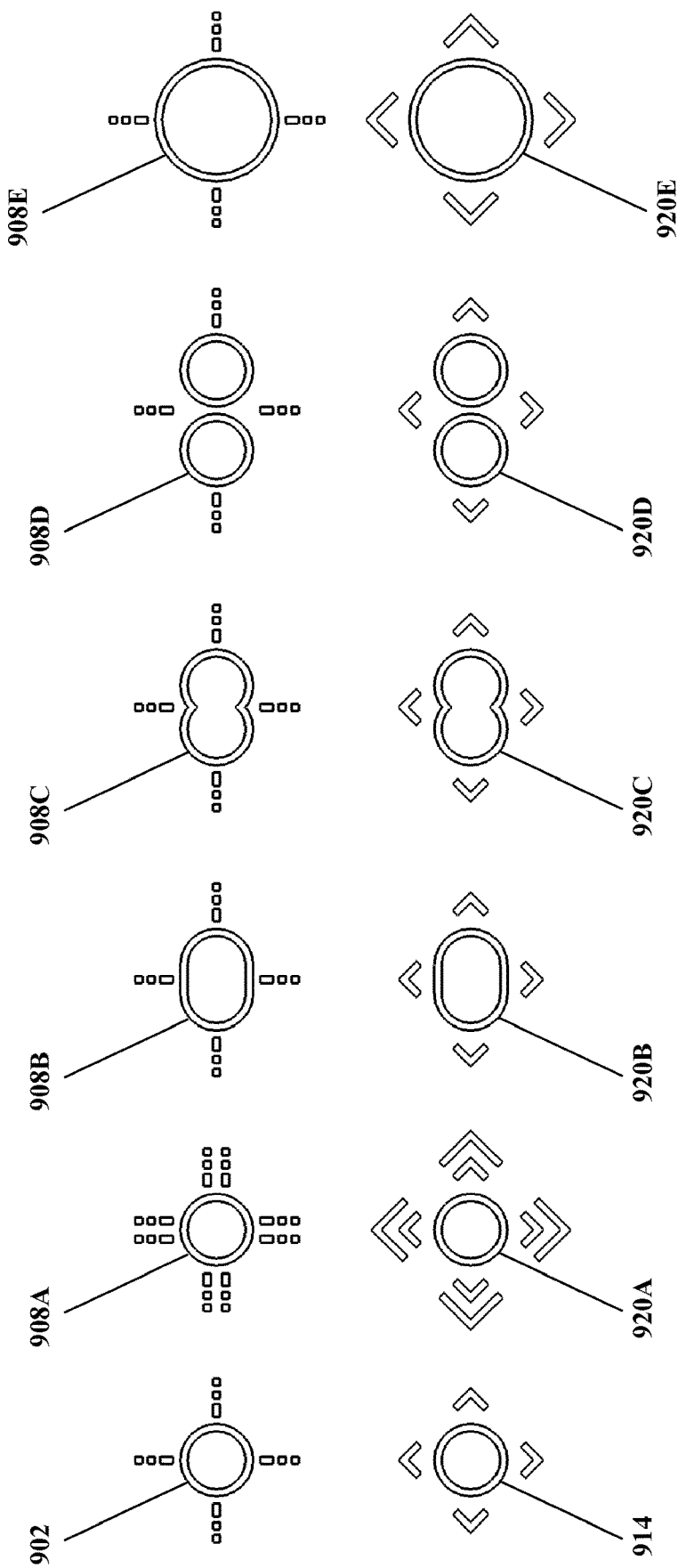
FIG. 9 shows example cursors in one-finger and two-finger variations, in graphical form.

Now with reference to FIG. 9, for at least certain embodiments it may be useful if cursors and/or forms thereof are graphically indicative of the user input(s) that are associated with those cursors and/or forms. Such graphic indications also may serve to distinguish different cursors and/or forms from one another, for example, a one-finger cursor from a two-finger cursor. However, the manner in which cursors may be so indicative and/or so distinctive may vary considerably, and the particular graphical details of examples shown and described herein are not limiting.

For example, FIG. 9 shows a one-finger general cursor 902 and a one-finger swipe cursor 914. The one-finger general cursor 902 and one-finger swipe cursor 914 may be considered to be base forms, although for purposes of illustration regarding the example of FIG. 9 the precise form(s) may not be of consequence.

In addition, FIG. 9 also shows several two-finger general cursors 908A through 908E and several two-finger swipe cursors 920A through 920E.

As may be seen, each of the two-finger general cursors 908A through 908E bear some graphical resemblance to the one-finger general cursor 902, and each of the two-finger swipe cursors 920A through 920E bear some graphical resemblance to the one-finger swipe cursor 914 (though each such two-finger cursor 908A through 908E and 920A through 920E still remains graphically distinct from the one-finger cursors 902 and 914, respectively). However, each two-finger cursor 908A through 908E and 920A through 920E bears graphical indication that, as compared with the one finger cursors 902 and 914, two fingers may be called for.

For example, as may be seen the one-finger general cursor 902 includes dashed crosshairs distributed at cardinal points around a circle, and the one-finger swipe cursor 914 includes arrows distributed at cardinal points around a circle. By contrast, the two-finger general cursor 908A includes pairs of dashed crosshairs, and two-finger swipe cursor 920A includes pairs of arrows. Such pairing may serve as a graphical indication of two-finger input.

Similarly, the one-finger general cursor 902 and the one-finger swipe cursor 914 each include a circle; by contrast, the two-finger general cursor 902B and the two-finger swipe cursor 914B include lozenge shapes in place of circles, broader across than circles. This may serve as graphical indication of two-finger input (e.g. two fingertips side by side as opposed to a single fingertip).

Likewise, the two-finger general cursor 902C and the two-finger swipe cursor 914C include two partial circles in contact with one another; the two-finger general cursor 902D and the two-finger swipe cursor 914D include two circles in proximity to one another; and the two-finger general cursor 902E and the two-finger swipe cursor 914E include larger circles than the one-finger general cursor 902 and the one-finger swipe cursor 914. Each such may serve as graphical indication of two-finger input.

Although FIG. 9 shows only one-finger general cursors, two-finger general cursors, one-finger swipe cursors, and two-finger swipe cursors, it should be understood that other cursors and/or forms thereof also may vary considerably while remaining graphically indicative of an associated input, and/or graphically distinct from other cursors and/or forms.

Figure 10:
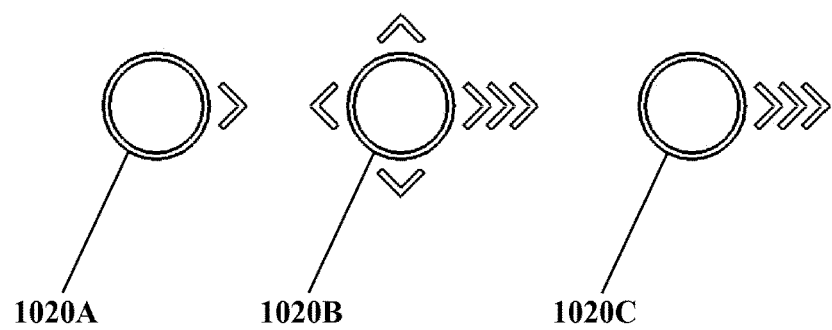
FIG. 10 shows example cursors exhibiting variations of swipe indications, in graphical form.

Similarly, with reference to FIG. 10, therein are shown three examples 1020A, 1020B, and 1020C of swipe cursors (which depending on the embodiment may be one-finger, two-finger, or non-specific as to fingers). As may be seen, swipe cursor 1020A includes a single arrow pointing to the right; swipe cursor 1020B shows a single arrow in three cardinal directions but three arrows to the right; and swipe cursor 1020C shows three arrows to the right. Each of the swipe cursors 1020A, 1020B, and 1020C may be graphically indicative of a swipe, and or of a swipe in a particular direction (e.g. to the right). However, even though all of the swipe cursors 1020A, 1020B, and 1020C in FIG. 10 include circles and arrows (which is not limiting), arrangements of the swipe cursors 1020A, 1020B, and 1020C may be seen to vary considerably.

It is noted that depending on embodiment the swipe cursors 1020A, 1020B, and 1020C in FIG. 10 may represent different forms. For example, the swipe cursors 1020A, 1020B, and 1020C may represent base forms prompting a user to swipe in a particular direction (e.g. to the right). However, the swipe cursors 1020A, 1020B, and 1020C also may represent engaged forms confirming to a user that a swipe in a particular direction (e.g. to the right) has been detected. Other arrangements also may be equally suitable.

Figure 11:
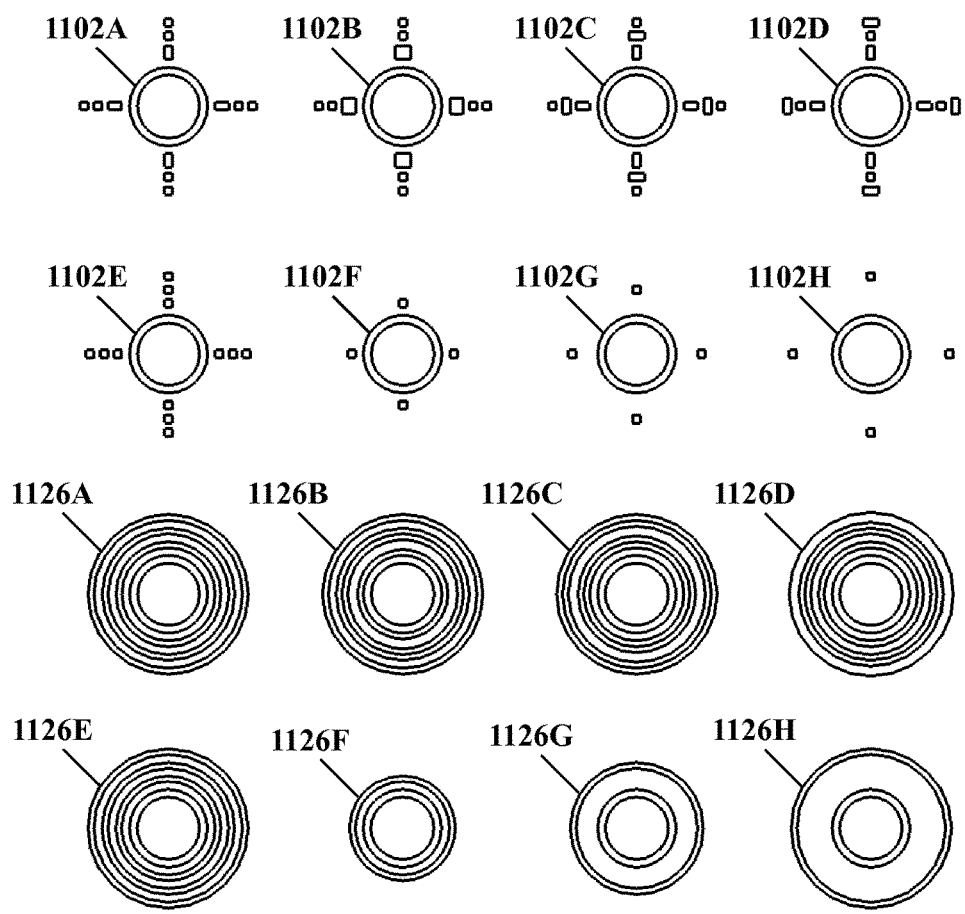
FIG. 11 shows example cursors exhibiting animations, in graphical form.
Figure 12:
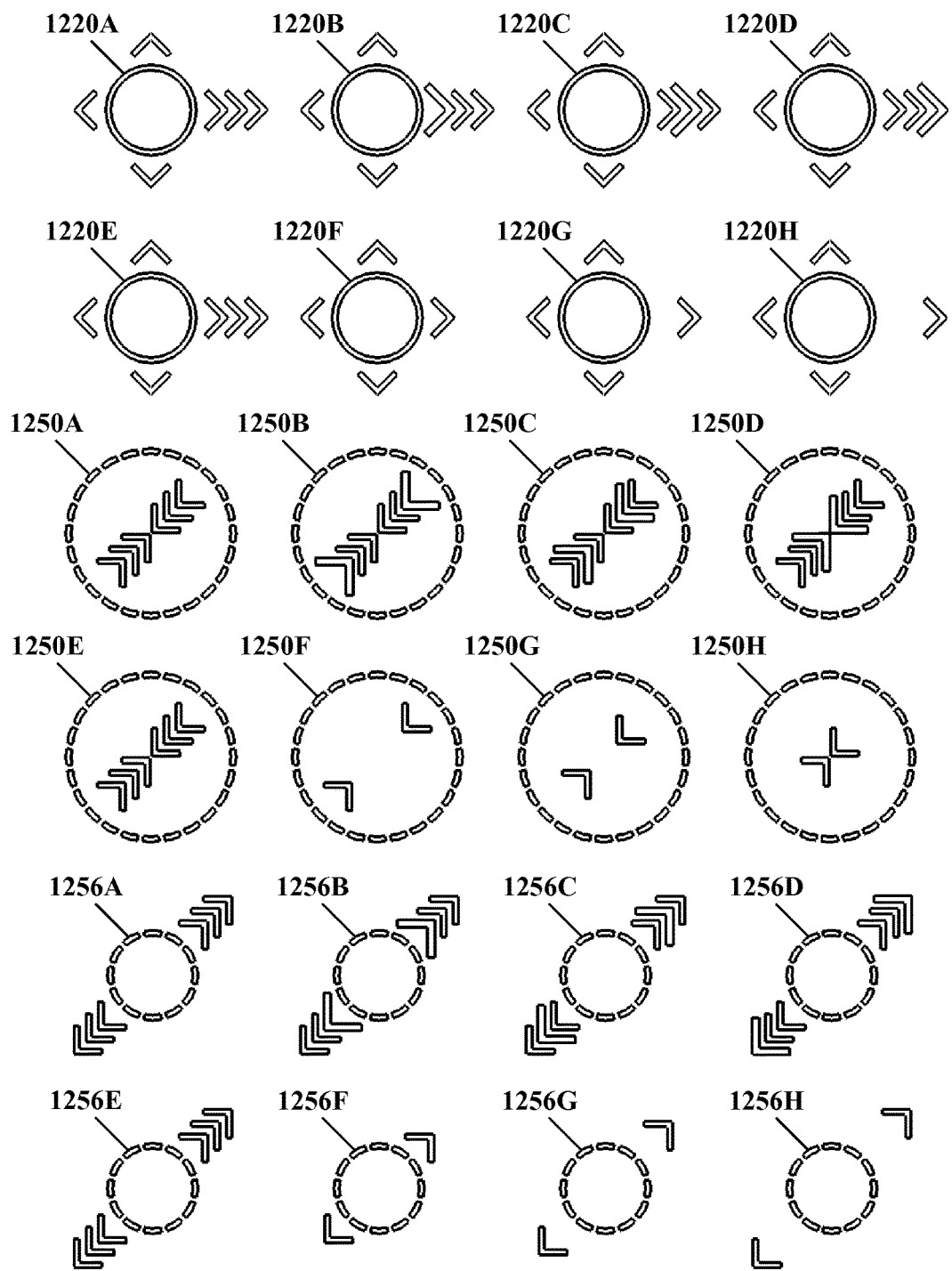
FIG. 12 shows further example cursors exhibiting animations, in graphical form.

Now with reference to FIG. 11 and FIG. 12, although line art illustrations herein of certain cursors and/or forms arrangements are inherently static and black-and-white (due to limitations of line art), cursors and/or forms are not necessarily so limited. It should be understood that cursors, forms, portions thereof, etc. may vary in color, shade, transparency, etc., and/or may be solid, hollow, patterned, etc. In addition, as shown in FIG. 11 and FIG. 12 cursors and/or forms may be animated.

For example, FIG. 11 shows a one-finger general cursor 1102A, including a circle with dashed crosshairs arranged in cardinal directions around the circle. Elements 1102B, 1102C, and 1102D show similar arrangements to one-finger general cursor 1102A, however in each of elements 1102B, 1102C, and 1102D one dash in each crosshair is widened. If elements 1102B, 1102C, and 1102D are taken as frames in an animation, the appearance may be that wide dashes are moving outward from the circle. Although increased width is shown for elements 1102B, 1102C, and 1102D, changes in brightness, color, or transparency, actual motion of dashes, etc. also may be suitable.

FIG. 11 also shows a one-finger general cursor 1102E, along with elements 1102F, 1102G, and 1102H. In each of elements 1102F, 1102G, and 1102H two of the dashes in each crosshair present in 1102E are absent. If elements 1102F, 1102G, and 1102H are taken as frames in an animation, the appearance may be that individual dashes are moving outward from the circle.

FIG. 11 shows a one-finger press-and-hold cursor 1126A, including a circle with three concentric rings. Elements 1126B, 1126C, and 1126D show similar arrangements to one-finger general cursor 1126A, however in each of elements 1126B, 1126C, and 1126D one of the concentric rings is widened. If elements 1126B, 1126C, and 1126D are taken as frames in an animation, the appearance may be that wide rings are moving outward from the circle.

FIG. 11 also shows also shows a one-finger press-and-hold cursor 1126E, along with elements 1126F, 1126G, and 1126H. In each of elements 1126F, 1102G, and 1126H two of the concentric rings present in 1126E are absent. If elements 1126F, 1126G, and 1126H are taken as frames in an animation, the appearance may be that individual dashes are moving outward from the circle.

Similarly, FIG. 12 shows a two-finger swipe cursor 1220A, including a circle with single arrows arranged in three cardinal directions around the circle and a group of three arrows extending to the right. Elements 1220B, 1220C, and 1220D show similar arrangements to 1220A, however in each of elements 1220B, 1220C, and 1220D one arrow in the group of three is enlarged. If elements 1220B, 1220C, and 1220D are taken as frames in an animation, the appearance may be that enlarged arrows are moving rightward from the circle.

FIG. 12 also shows a two-finger swipe cursor 1220E. Elements 1220F, 1220G, and 1220H show similar arrangements to 1220E, however in each of elements 1220F, 1220G, and 1220H two of the arrows present in the group of three in 1220E are missing. If elements 1220F, 1220G, and 1220H are taken as frames in an animation, the appearance may be that arrows are moving rightward from the circle.

FIG. 12 shows a pinch in cursor 1250A, including a dashed circle enclosing two sets of three arrows pointing inward. Elements 1250B, 1250C, and 1250D show similar arrangements to 1250A, however in each of elements 1250B, 1250C, and 1250D one arrow in each group of three is enlarged. If elements 1250B, 1250C, and 1250D are taken as frames in an animation, the appearance may be that enlarged arrows are moving inward toward the middle of the dashed circle.

FIG. 12 also shows a pinch in cursor 1250E. Elements 1250F, 1250G, and 1250H show similar arrangements to 1250E, however in each of elements 1250F, 1250G, and 1250H two of the arrows present in each group of three in 1250E are missing. If elements 1250F, 1250G, and 1250H are taken as frames in an animation, the appearance may be that arrows are moving inward toward the middle of the dashed circle.

FIG. 12 shows a pinch out cursor 1256A, including a dashed circle within two sets of three arrows pointing outward. Elements 1256B, 1256C, and 1256D show similar arrangements to 1256A, however in each of elements 1256B, 1256C, and 1256D one arrow in each group of three is enlarged. If elements 1256B, 1256C, and 1256D are taken as frames in an animation, the appearance may be that enlarged arrows are moving outward from the dashed circle.

FIG. 12 also shows a pinch out cursor 1256E. Elements 1256F, 1256G, and 1256H show similar arrangements to 1256E, however in each of elements 1256F, 1256G, and 1256H two of the arrows present in each group of three in 1256E are missing. If elements 1256F, 1256G, and 1256H are taken as frames in an animation, the appearance may be that arrows are moving outward from the dashed circle.

FIG. 11 and FIG. 12 are examples only. Animations other than what is shown in FIG. 11 and FIG. 12 may be equally suitable. For example, although the dashed circles in cursors 1250A through 1250H and 1256A through 1256H are shown with constant size, in certain embodiments the dashed circles may change responsive to user input, for example increasing in size if the user moves his or her fingers apart (i.e. pinching in) or decreasing in size if the user moves his or her fingers together (i.e. pinching in).

In addition, animation is not required to be present. Where animation is present, animation is not required to be uniform or universal (nor are other features or changing features such as color, transparency, etc.). Certain cursors and/or forms of cursors may be animated while others are not. For example, a hover form and/or an engaged form of a cursor may be animated, while the base form of the same cursor is static, for example. Such variation may serve as a graphical distinction between different cursors and/or forms, may provide emphasis, may draw attention to certain cursors or forms over others, may serve as confirmation to a user that a hover or an input is detected, etc.

Figure 13:
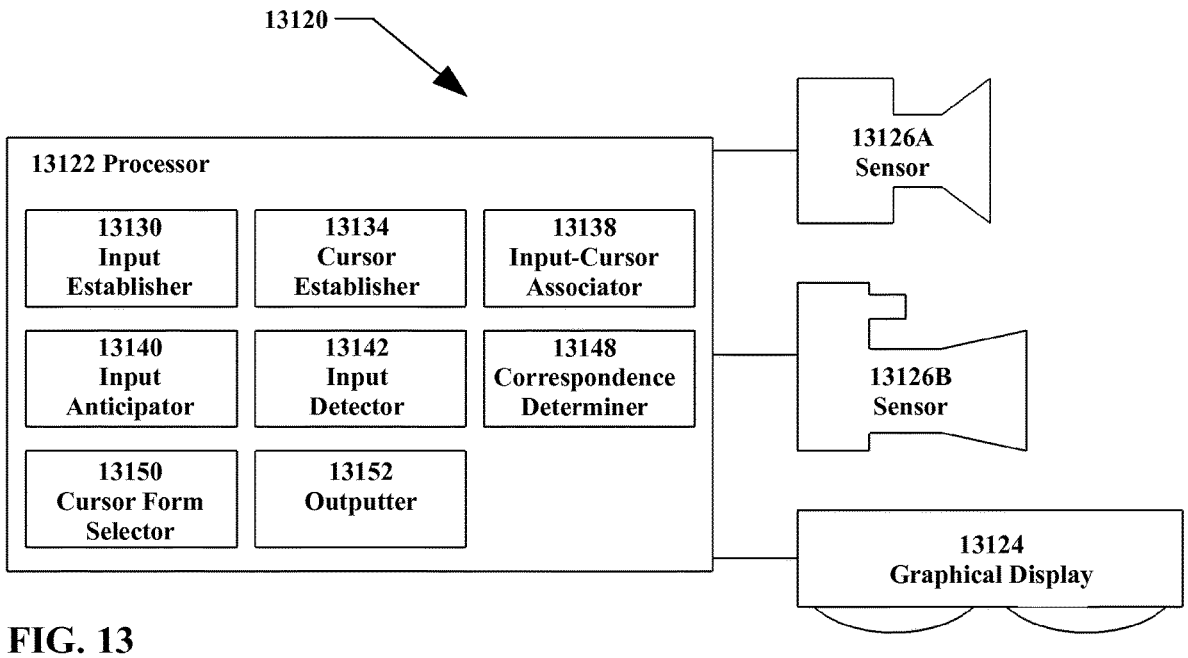
FIG. 13 shows an example integral apparatus for interface control with prompt and feedback, in schematic form.

Now with reference to FIG. 13, therein is shown an example embodiment of an apparatus 13120 for interface control with prompt and feedback. As shown, the apparatus 13120 includes a processor 13122, adapted to execute executable instructions instantiated thereon. The processor 13122 is not limited with regard to form, structure, etc. The processor 13122 may, for example, be a digital electronic processor, such as may be present in a head-mounted display, smartphone, tablet, laptop computer, desktop computer, etc., but other arrangements also may be suitable.

The apparatus 13120 also includes a graphical display 13124. As shown the graphical display 13124 is a stereo display, but this is not limiting and other arrangements may be suitable. Embodiments are not limited with regard to the form, structure, etc. of the graphical display 13124. For example, the graphical display 13124 may include LED or OLED displays, CRT displays, plasma displays, laser displays, etc., though other arrangements may be equally suitable.

In addition, the example apparatus 13120 as-illustrated also includes sensors 13126A and 13126B. In FIG. 13 the sensors 13126A and 13126B are illustrated as an RGB imager and a depth imager respectively, but this is an example only. The sensors 13126A and 13126B may serve for example to detect and/or assist in detecting inputs, hovers, etc., for example by acquiring data and providing that data to the processor 13122 and/or to executable instructions instantiated thereon.

Still with reference to FIG. 13, as may be seen a number of entities 13130 through 13152 are shown disposed on the processor 13122. The entities 13130 through 13152 may include executable instructions instantiated on the processor, non-executable data, some combination thereof, etc. With regard to the example shown in FIG. 13 the entities 13130 through 13152 are described as including data and/or executable instructions and may be considered as being data entities, but other arrangements may be equally suitable.

Although data entities 13130 through 13152 are shown as being distinct for clarity (e.g. so as to indicate certain functions), this is an example only. Data entities may be combined, subdivided, disposed on multiple processors and/or clouds, otherwise reorganized, etc. Furthermore, where functions are not required certain of the data entities 13130 through 13152 may be eliminated, or additional data entities added, in various embodiments.

With regard individually to the data entities 13130 through 13152, an input establisher 13130 is disposed on the processor 13122, and is adapted to establish inputs, for example defining hand gestures that when received will serve as or invoke processor commands, executable instructions, etc.

A cursor establisher 13134 is disposed on the processor 13122 and is adapted to establish graphical cursors and/or forms thereof. An input-cursor associator 13138 is disposed on the processor 13122 and is adapted to associate inputs with cursors, such that an input or group of inputs is associated with some cursor. For example, one-finger hand gesture inputs may be associated with a graphically distinctive one-finger cursor, while two-finger hand gesture inputs may be associated with a graphically distinctive two-finger cursor.

An input anticipator 13140 is disposed on the processor 13122, and is adapted to establish one or more anticipated inputs, anticipated inputs, for example, being suited for current conditions (e.g. inputs for manipulating a 3D model when a 3D model is being displayed), or otherwise considered likely to be entered and/or required, etc.

An input detector 13142 is disposed on the processor 13122 and is adapted to detect inputs. For example, for inputs in the form of user hand gestures, the input detector may be adapted to identify hand positions, hand motions, hand configurations, etc. in RGB images and depth images as received from the sensors 13126A and 13126B, though this is an example only and is not limiting.

A correspondence determiner 13148 is disposed on the processor 13122 and is adapted to determine whether detected inputs correspond with anticipated inputs.

A cursor form selector 13150 is disposed on the processor 13122 and is adapted to select a cursor and/or a form thereof, for example, based on the status of and/or communications from others of the entities 13130 through 13152. As a more concrete example, based on anticipated inputs determined by the input anticipator 13140, the cursor form selector

13150 may select a base form of a one-finger general cursor if the input anticipator 13140 determines that the one-finger general cursor is the (or an) anticipated input. Similarly, the cursor form selector 13150 may select an engaged form of the one-finger general cursor if the correspondence determiner 13148 determines that detected input matches the anticipated input (in this example, that a one-finger input was detected when the one-finger input was anticipated).

An outputter 13152 is disposed on the processor 13122 and is adapted to output cursors and/or forms thereof to the graphical display 13124. For example, cursors and/or forms as selected by the cursor form selector 13150 may be communicated to the outputter 13152, which then sends the selected cursors and/or forms to the graphical display 13124.

As may be seen, the arrangement in FIG. 13 does not refer specifically to any particular cursors and/or forms. Unless otherwise specified, individual embodiments are not necessarily limited to any particular cursors or forms, or to any particular prompts, feedback, or variations thereof.

Although not shown in the example apparatus 13120 shown in FIG. 13, embodiments may include additional elements, such as a data store, a communicator, etc. Such elements may serve to support certain functions described herein, for example, cursors may be established by being read from a data store, received from some external source via a communicator, etc.

Figure 14:
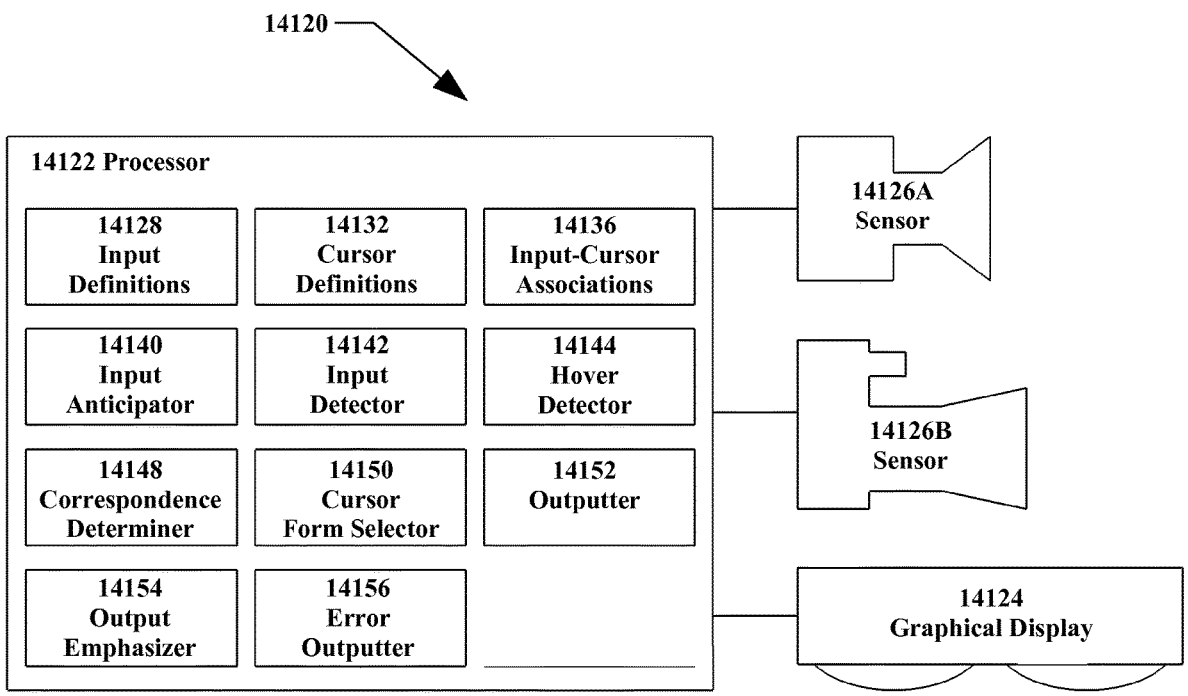
FIG. 14 shows another example integral apparatus for interface control with prompt and feedback, in schematic form.

In addition, with reference now to FIG. 14 embodiments may vary considerably in terms of elements and functions. In the example arrangement of FIG. 14, an apparatus 14120 again is shown, again with a processor 14120, graphical display 14124, and sensors 14126A and 14126B. A number of data entities 14128 through 14156 again are shown disposed on the processor 14122, however, the particular entities 14128 through 14156 and functions performed thereby differ from the arrangement in FIG. 13.

In FIG. 14, input definitions 14128 are disposed on the processor 14122. Where in FIG. 13 an input establisher 13130 was instantiated onto the processor 13122 so as to establish inputs, in FIG. 14 input definitions 14128 are themselves instantiated on the processor 14122. The distinction may be considered one of providing a tool for producing a product in FIG. 13, and providing the product itself in FIG. 14. Yet other arrangements also may be equally suitable.

Likewise, cursor definitions 14128 are disposed on the processor 14122, and input-cursor associations 14128 are disposed on the processor 14122.

An input anticipator 14128 is disposed on the processor 14122 and is adapted to establish one or more inputs. An input detector 14128 is disposed on the processor 14122 and is adapted to detect inputs.

A hover detector is disposed on the processor 14122 and is adapted to detect hovers associated with (e.g. preliminary to) inputs. For example, for inputs in the form of user hand gestures, the input detector may be adapted to identify hand positions, hand motions, hand configurations, etc. in RGB images and depth images as received from the sensors 13126A and 13126B so as to determine whether a hover is taking place, e.g. whether the user's hand is "hovering" over a cursor, whether the user's hand is about to enter an input to the cursor, etc., though this is an example only and is not limiting.

A correspondence determiner 14128 is disposed on the processor 14122, and is adapted to determine correspondence among anticipated inputs, detected inputs, detected hovers, etc.

A cursor form selector 14128 is disposed on the processor 14122 and is adapted to select a cursor and/or a form thereof, for example, based on the status of and/or communications from others of the entities 14128 through 14156. An outputter 14128 is disposed on the processor 14122 and is adapted to output cursors and/or forms thereof to the graphical display 14124.

An output emphasizer 14128 is disposed on the processor 14122 and is adapted to emphasize cursors and/or forms thereof output to the graphical display (whether by communicating with the outputter 14152 to address forms/cursors before output, communicating with the graphical display 14124 directly, or otherwise). For example, the output emphasizer may alter the color, size, brightness, transparency, animation, etc. of a cursor or form thereof, for example in response to a mismatch between what inputs are anticipated and what inputs are detected.

An error outputter 14128 is disposed on the processor 14122 and is adapted to output error indications to the graphical display (again whether by communicating with the outputter 14152 to add error indications to forms/cursors before output, communicating with the graphical display 14124 directly, or otherwise). As noted, error indications, output emphasis, and error forms of cursors may to some degree overlap, thus even when error outputs exist the error outputs may be handled by an output emphasizer 14154 or a cursor form selector 14150 rather than necessarily by a distinct error outputter 14156.

Figure 15:
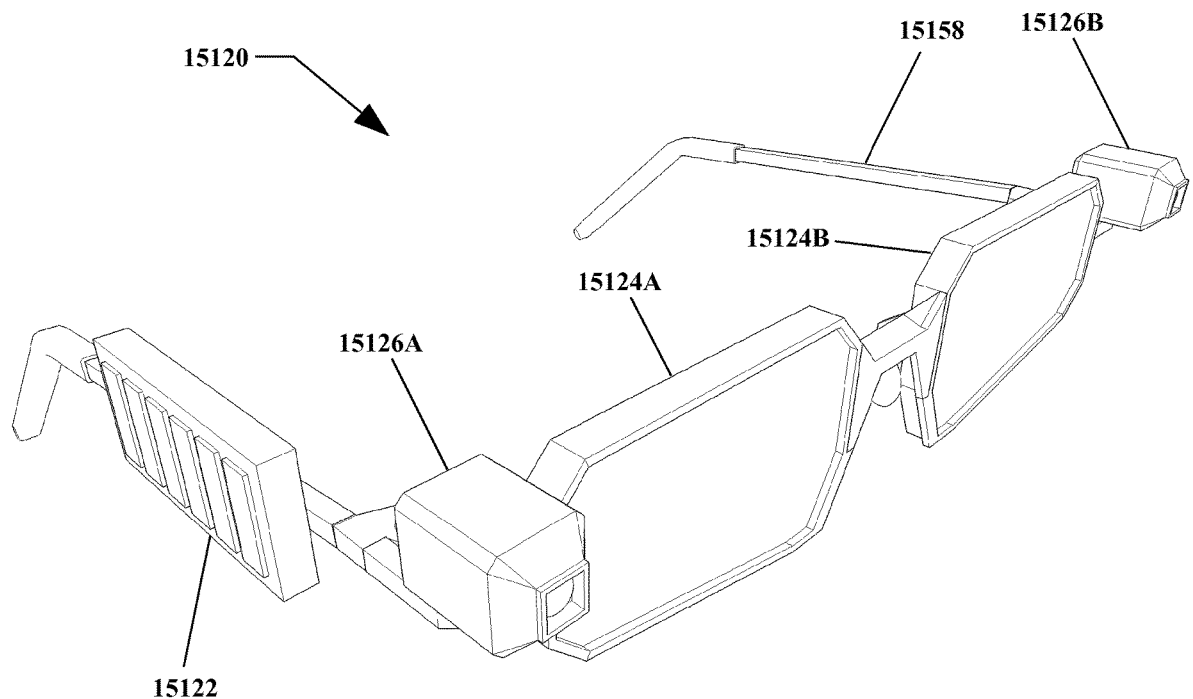
FIG. 15 shows an example integral apparatus for interface control with prompt and feedback, in perspective view.

Turning now to FIG. 15, therein an example apparatus 15120 is shown in perspective view. In the example arrangement shown in FIG. 15 the apparatus 15120 includes a frame 15158, the frame 15158 being in the form of a head-mounted display resembling a pair of glasses. However, this arrangement is not limiting, and other arrangements may be equally suitable.

The apparatus includes a processor 15122, sensors 15126A and 15126B, and displays 15124A and 15124B in a stereo configuration (which alternatively may be considered as a single display), disposed on the frame 15158. As may be seen, the displays 15124A and 15124B are configured on the frame 15158 such that when the apparatus 15120 is worn by a user, the displays 15124A and 15124B may be disposed facing and proximate the user's eyes. Also, when the apparatus 15120 is worn the sensors 15126A and 15126B are forward facing relative to the user (and/or the user's head/face), and depending upon the particulars of the sensors 15126A and 15126B may exhibit fields of view directed forward and potentially similar to the fields of view of the user's eyes.

Figure 16:
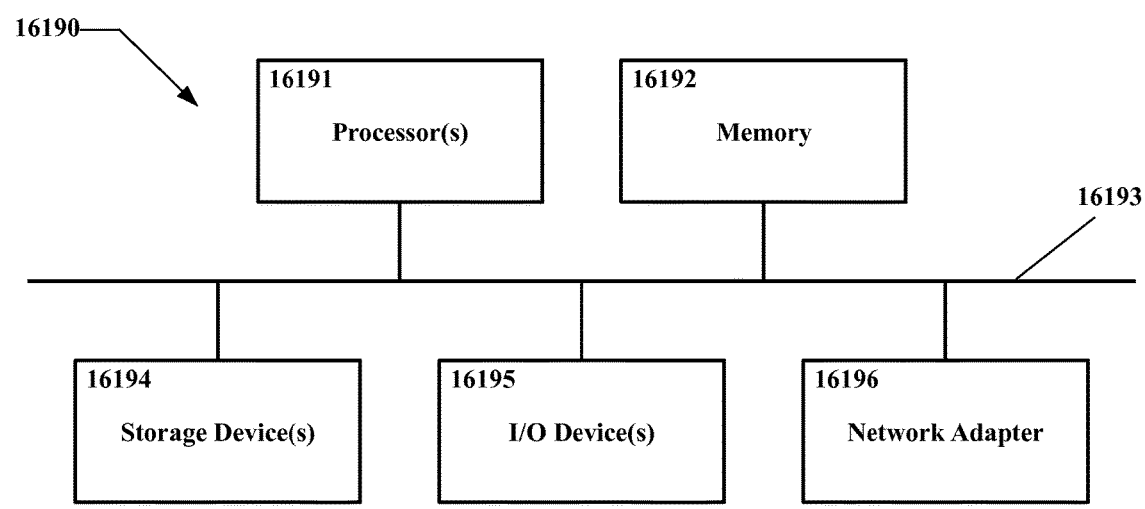
FIG. 16 shows a block diagram of a processing system that may implement operations of various embodiments.

FIG. 16 is a block diagram of an apparatus that may perform various operations, and store various information generated and/or used by such operations, according to an embodiment of the disclosed technique. The apparatus may represent any computer or processing system described herein. The processing system 16190 is a hardware device on which any of the other entities, components, or services depicted in the examples of FIG. 1 through FIG. 15 (and any other components described in this specification) may be implemented. The processing system 16190 includes one or more processors 16191 and memory 16192 coupled to an interconnect 16193. The interconnect 16193 is shown in FIG. 16 as an abstraction that represents any one or more separate physical buses, point to point connections, or both connected by appropriate bridges, adapters, or controllers. The interconnect 16193, therefore, may include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also called "Firewire".

The processor(s) 16191 is/are the central processing unit of the processing system 16190 and, thus, control the overall operation of the processing system 16190. In certain embodiments, the processor(s) 16191 accomplish this by executing software or firmware stored in memory 16192. The processor(s) 16191 may be, or may include, one or more programmable general-purpose or special-purpose microprocessors, digital signal processors (DSPs), programmable controllers, application specific integrated circuits (ASICs), programmable logic devices (PLDs), trusted platform modules (TPMs), or the like, or a combination of such devices.

The memory 16192 is or includes the main memory of the processing system 16190. The memory 16192 represents any form of random access memory (RAM), read-only memory (ROM), flash memory, or the like, or a combination of such devices. In use, the memory 16192 may contain a code. In one embodiment, the code includes a general programming module configured to recognize the general-purpose program received via the computer bus interface, and prepare the general-purpose program for execution at the processor. In another embodiment, the general programming module may be implemented using hardware circuitry such as ASICs, PLDs, or field-programmable gate arrays (FPGAs).

The network adapter 16194, a storage device(s) 16195, and I/O device(s) 16196 are also connected to the processor(s) 16191 through the interconnect 16193. The network adapter 16194 provides the processing system 16190 with the ability to communicate with remote devices over a network and may be, for example, an Ethernet adapter or Fibre Channel adapter. The network adapter 16194 may also provide the processing system 16190 with the ability to communicate with other computers within the cluster. In some embodiments, the processing system 16190 may use more than one network adapter to deal with the communications within and outside of the cluster separately.

The I/O device(s) 16196 can include, for example, a keyboard, a mouse or other pointing device, disk drives, printers, a scanner, and other input and/or output devices, including a display device. The I/O device(s) 16196 also may include, for example, cameras and/or other imagers adapted to accept visual input including but not limited to postures and/or gestures. The display device may include, for example, a cathode ray tube (CRT), liquid crystal display (LCD), or some other applicable known or convenient display device. The display device may take various forms, including but not limited to stereo displays suited for use in near-eye applications such as head mounted displays or other wearable devices.

The code stored in memory 16192 may be implemented as software and/or firmware to program the processor(s) 16191 to carry out actions described herein. In certain embodiments, such software or firmware may be initially provided to the processing system 16190 by downloading from a remote system through the processing system 16190 (e.g., via network adapter 16194).

The techniques herein may be implemented by, for example, programmable circuitry (e.g. one or more microprocessors) programmed with software and/or firmware, or entirely in special-purpose hardwired (non-programmable) circuitry, or in a combination of such forms. Special-purpose hardwired circuitry may be in the form of, for example, one or more ASICs, PLDs, FPGAs, etc.

Software or firmware for use in implementing the techniques introduced here may be stored on a machine-readable storage medium and may be executed by one or more general-purpose or special-purpose programmable microprocessors. A "machine-readable storage medium", as the term is used herein, includes any mechanism that can store information in a form accessible by a machine.

A machine can also be a server computer, a client computer, a personal computer (PC), a tablet PC, a laptop computer, a set-top box (STB), a personal digital assistant (PDA), a cellular telephone, an iPhone, a Blackberry, a processor, a telephone, a web appliance, a network router, switch, or bridge, or any machine capable of executing a set of instructions (sequential or otherwise) that specify actions to be taken by that machine.

A machine-accessible storage medium or a storage device(s) 16195 includes, for example, recordable/non-recordable media (e.g., ROM; RAM; magnetic disk storage media; optical storage media; flash memory devices; etc.), etc., or any combination thereof. The storage medium typically may be non-transitory or include a non-transitory device. In this context, a non-transitory storage medium may include a device that is tangible, meaning that the device has a concrete physical form, although the device may change its physical state. Thus, for example, non-transitory refers to a device remaining tangible despite this change in state.

The term "logic", as used herein, may include, for example, programmable circuitry programmed with specific software and/or firmware, special-purpose hardwired circuitry, or a combination thereof.

The above specification, examples, and data provide a complete description of the manufacture and use of the composition of the invention. Since many embodiments of the invention can be made without departing from the spirit and scope of the invention, the invention resides in the claims hereinafter appended.

The invention claimed is:

1. A method, comprising:
    associating, by a processing device, a first graphical cursor with a first type of gesture;
    associating, by the processing device, a second graphical cursor with a second type of gesture, wherein the first graphical cursor and the second graphical cursor are graphically distinct from each other;
    associating, by the processing device, a first virtual object with the first graphical cursor and the first type of gesture, wherein the first type of gesture is an interaction with the first virtual object;
    anticipating, by the processing device, detecting the first type of gesture at a first point in time;
    displaying, by a head-mounted display, the first virtual object with the first graphical cursor;
    displaying a first base form of the first graphical cursor:
    detecting, by a sensor, a first viewer input from a viewer of the head-mounted display;
    determining, by the processing device, whether a form of the first viewer input detected by the sensor is:
        a first appearance that indicates the viewer is preparing to initiate the first type of gesture;
        a second appearance that indicates the viewer is preparing to initiate the second type of gesture; or
        a third appearance that indicates the viewer is preparing to initiate an unknown type of gesture;
    in response to the first viewer input indicating the viewer is preparing to initiate the second type of gesture or the unknown type of gesture, displaying, by the head-mounted display, a first indicator that the first type of gesture is anticipated; and iteratively detecting the first viewer input by the sensor and displaying, by the head-mounted display, the first indicator until the first viewer input indicates the viewer is preparing to initiate the first type of gesture; and in response to the first viewer input indicating the viewer is preparing to initiate the first type of gesture, displaying a confirmation that the first viewer input corresponds to the anticipated first type of gesture, wherein the confirmation comprises an engaged form of the graphical cursor.

2. The method of claim 1, wherein:
the first graphical cursor comprises a first hover form, or a first engaged form; and
the second graphical cursor comprises a second base form that is different than the first base form, a second hover form that is different than the first hover form, or a second engaged form that is different than the first engaged form.

3. The method of claim 1, further comprising, in response to the first viewer input indicating the viewer is preparing to initiate the first type of gesture, displaying, by the head-mounted display, a second indicator that the first viewer input is a correct form of input.

4. The method of claim 1, wherein the first type of gesture is a hand gesture performed in a free space removed from a physical surface.

5. The method of claim 1, further comprising, in response to the first viewer input indicating the viewer is preparing to initiate the second type of gesture or the unknown type of gesture, displaying, by the head-mounted display, a graphical emphasis of a portion of the first graphical cursor indicating a non-correspondence between the anticipated first type of gesture and the first viewer input detected by the sensor.

6. The method of claim 1, wherein the first indicator is an error indication that indicates to the viewer a non-correspondence between the first viewer input detected by the sensor and the first type of gesture.

7. The method of claim 1, further comprising:
associating, by the processing device, a second virtual object with the first graphical cursor and the first type of gesture, wherein the first type of gesture is an interaction with the second virtual object;
displaying, by the head-mounted display, the second virtual object with the first graphical;
detecting, by the sensor, a second viewer input from the viewer of the head-mounted display;
determining whether a form of the second viewer input detected by the sensor is:
a fourth appearance that indicates the viewer is preparing to initiate the first type of gesture;
a fifth appearance that indicates the viewer is preparing to initiate the second type of gesture; or
a sixth appearance that indicates the viewer is preparing to initiate the unknown type of gesture;
in response to the second viewer input indicating the viewer is preparing to initiate the second type of gesture or the unknown type of gesture, displaying, by the head-mounted display, a second indicator that the first type of gesture is anticipated; and
iteratively detecting the second viewer input and displaying the second indicator until the second viewer input indicates the viewer is preparing to initiate the first type of gesture.

8. The method of claim 1, further comprising:
associating, by the processing device, the first virtual object with the second graphical cursor and the second type of gesture, wherein the second type of gesture is another interaction with the first virtual object;
anticipating, by the processing device, detecting the second type of gesture at a second point in time that is after the first point in time;
displaying, by the head-mounted display, the first virtual object with the second graphical cursor;
detecting, by the sensor, a second viewer input from the viewer of the head-mounted display;
determining whether a form of the second viewer input detected by the sensor is:
a fourth appearance that indicates the viewer is preparing to initiate the first type of gesture;
a fifth appearance that indicates the viewer is preparing to initiate the second type of gesture; or
a sixth appearance that indicates the viewer is preparing to initiate the unknown type of gesture;
in response to the second viewer input indicating the viewer is preparing to initiate the first type of gesture or the unknown type of gesture, displaying, by the head-mounted display, a second indicator that the second type of gesture is anticipated; and
iteratively detecting the second viewer input and displaying the second indicator until the second viewer input indicates the viewer is preparing to initiate the second type of gesture.

9. The method of claim 1, wherein the first type of gesture or the second type of gesture is defined by:
a degree of finger separation between fingers of a hand of the viewer;
a bend in a knuckle of the hand;
a curve in a motion path of the hand or a finger of the hand; or
a direction of the motion path.

10. The method of claim 9, wherein the unknown type of gesture is defined by:
the degree of finger separation between the fingers of the hand of the viewer exceeding a defined threshold for the degree of finger separation;
the bend in the knuckle of the hand exceeding a defined threshold for the bend in the knuckle;
the curve in the motion path of the hand or the finger of the hand being different from a defined curve for the motion path of the hand or the finger; or
the direction of the motion path being different than a defined direction for the motion path.

11. The method of claim 1, wherein the first graphical cursor or the second graphical cursor comprises:
a hollow circle with dashed crosshair marks disposed around a periphery thereof;
a hollow circle with contracted dashed crosshair marks disposed around a periphery thereof;
a filled circle;
a filled circle with at least one concentric circle thereabout;
a hollow circle with arrow marks disposed around a periphery thereof;
a filled circle with arrow marks disposed around a periphery thereof;
a filled circle with arrow marks disposed around a periphery thereof with at least one of the arrow marks comprising at least two arrows;
a hollow dashed circle with arrow marks disposed around a periphery thereof and pointing outward therefrom;

a filled dashed circle with arrow marks disposed around a periphery thereof and pointing outward therefrom with each of the arrow marks comprising at least two arrows;

a hollow dashed circle with arrow marks disposed within a periphery thereof and pointing inward therefrom; or a filled dashed circle with arrow marks disposed within a periphery thereof and pointing inward therefrom with each of the arrow marks comprising at least two arrows.

12. The method of claim 1, wherein:
the first graphical cursor comprises a first base form and a first non-base form; or
the second graphical cursor comprises a second base form and a second non-base form.

13. The method of claim 1, wherein the first type of gesture is a single finger gesture and the second type of gesture is a multiple finger gesture.

14. The method of claim 1, wherein the first graphical cursor or the second graphical cursor comprises a hover form or a base form.

15. A device, comprising:
a wearable display configured to display a virtual object;
a sensor configured to detect a viewer input from a viewer of the wearable display;
a processing device coupled to the wearable display and the sensor, wherein the processing device is configured to:
  establish a first type of gesture for interacting with objects in a virtual reality environment;
  establish a second type of gesture for interacting with the objects in the virtual reality environment;
  associate a first virtual object with the first type of gesture, wherein the first type of gesture is an interaction with the first virtual object;
  anticipate detecting the first type of gesture;
  display, by the wearable display, the first virtual object;
  display a base form of a graphical cursor, the graphical cursor associated with the first type of gesture;
  detect, by the sensor, a first viewer input from the viewer of the wearable display;
  determine whether a form of the first viewer input detected by the sensor is:
    a first appearance that indicates the viewer is preparing to initiate the first type of gesture;
    a second appearance that indicates the viewer is preparing to initiate the second type of gesture; or
    a third appearance that indicates the viewer is preparing to initiate an unknown type of gesture; and
  in response to the first viewer input indicating the viewer is preparing to initiate the first type of gesture, display a confirmation that the first viewer input corresponds to the anticipated first type of gesture.

wherein the confirmation comprises an engaged form of the graphical cursor.

16. The device of claim 15, wherein the processing device is further configured to, in response to the first viewer input indicating the viewer is pre paring to initiate the second type of gesture or the unknown type of gesture, display, by the wearable display, an indicator that the first type of gesture is anticipated.

17. The device of claim 16, wherein the processing device is further configured to iteratively detect the first viewer input and display the indicator until the first type of gesture is detected by the sensor.

18. An apparatus, comprising:
a display configured to display a virtual object;
a sensor configured to detect an input from a viewer of the display;
a processing device coupled to the display and the sensor, wherein the processing device is configured to:
  associate a first virtual object with a first gesture, wherein the first gesture is an interaction with a first virtual object;
  associate the first gesture with a first cursor;
  display, by the display, the first virtual object;
  display a base form of the first cursor, the first cursor associated with the first aesture;
  detect, by the sensor, a viewer input from the viewer of the display; determine whether a form of the viewer input detected by the sensor is:
    a first appearance that indicates the viewer is about to initiate the first gesture; or
    a second appearance that indicates the viewer is about to initiate a second gesture; and
  in response to the form of the viewer input indicating the viewer is about to initiate the first gesture, display a confirmation the viewer is about to initiate a correct gesture for the first virtual object, wherein the confirmation comprises an engaged form of the first cursor.

19. The apparatus of claim 18, wherein the processing device is further configured to:
associate the second gesture with a second cursor, wherein the first cursor and the second cursor are visually distinct from each other; and
indicate to the viewer the first gesture is anticipated by displaying the first cursor with the virtual object.

20. The apparatus of claim 18, wherein the processing device is configured to iteratively detect the viewer input and display an indicator that the viewer input is an incorrect form until the form of the viewer input indicates the viewer is about to initiate the first gesture.

* * * * *